United States Patent
Lindemann et al.

(10) Patent No.: US 7,993,907 B2
(45) Date of Patent: Aug. 9, 2011

(54) BIOCHIPS AND METHOD OF SCREENING USING DRUG INDUCED GENE AND PROTEIN EXPRESSION PROFILING

(75) Inventors: Garrett W. Lindemann, Benicia, CA (US); John Lipani, Fountain Hills, AZ (US)

(73) Assignee: Mowycal Lending, LLC, Big Horn, WY (US)

( * ) Notice: Subject to any disclaimer, the term of this patent is extended or adjusted under 35 U.S.C. 154(b) by 625 days.

(21) Appl. No.: 10/140,680

(22) Filed: May 8, 2002

(65) Prior Publication Data

US 2003/0124552 A1 Jul. 3, 2003

Related U.S. Application Data

(60) Provisional application No. 60/289,407, filed on May 8, 2001.

(51) Int. Cl.
*C12Q 1/68* (2006.01)
*C07H 21/04* (2006.01)
*C12M 1/34* (2006.01)

(52) U.S. Cl. ........ 435/287.2; 435/6; 536/23.1; 536/24.1
(58) Field of Classification Search ...... 435/6; 436/518; 536/23.1; 702/19
See application file for complete search history.

(56) References Cited

U.S. PATENT DOCUMENTS

| | | | | |
|---|---|---|---|---|
| 5,863,779 | A | 1/1999 | Lal et al. | 435/193 |
| 6,197,599 | B1 * | 3/2001 | Chin et al. | 436/518 |
| 6,322,976 | B1 | 11/2001 | Aitman et al. | 435/6 |
| 6,326,180 | B1 | 12/2001 | Wei et al. | 435/189 |
| 6,346,381 | B1 | 2/2002 | Cohen et al. | 435/6 |
| 6,383,789 | B1 | 5/2002 | Webster et al. | 435/193 |

OTHER PUBLICATIONS

Amler et al., Cancer Research, vol. 60, pp. 6134-6141, Nov. 1, 2000.*
MacBeath et al., Science, vol. 289, pp. 1760-1763, 2000.*
Feng et al., Molecular Endocrinology, vol. 14, pp. 947-955, 2000.*

* cited by examiner

*Primary Examiner* — Shubo Zhou
(74) *Attorney, Agent, or Firm* — Lathrop & Gage LLP

(57) ABSTRACT

The present invention provides a biochip microarray, with multiple properties for use in identification of gene- and protein-induction or repression by drugs, the evaluation of efficacy and toxicity of any drug of choice, prediction of efficacy and toxicity of newly-discovered drugs, families of drugs or classes of drugs. Experimental information acquired from the biochip is inputted into a Drug-Gene-Protein-Biology (DGPB) database from which experimental data can be mined and analyzed based on the users preferences. A method for predicting the effect of a test composition for the treatment of a disease also is described. An animal model for the disease is selected. A biochip array for evaluating the effect of the test composition for the treatment of the disease is provided. The test composition is tested in the animal model to obtain a first set of biological markers representative of the effect of the test composition in the animal model. The biochip array generates a first set of data representative of the first set of biological markers. The first set of data is evaluated to predict the effect of the test composition on the disease. Preferably, the animal model is a standard animal model for human disease.

6 Claims, 2 Drawing Sheets

BIOCHIPS AND METHOD OF SCREENING USING DRUG INDUCED GENE AND PROTEIN EXPRESSION PROFILING

This application claims priority to U.S. Ser. No. 60/289,407, filed May 8, 2001.

BACKGROUND OF THE INVENTION

1. Field of the Invention

The present invention provides for a powerful method for identification of gene- and protein-induction by drugs in molecular pathways at both the cellular and whole animal level. In particular, the invention relates to a biochip microarray, wherein experimental information is loaded into a computer database which allows for mining of data, analysis of data for the predictability, evaluation of efficacy and toxicity of newly-discovered drugs, existing drugs, families of drugs or classes of drugs. The present invention drastically reduces the cost and time associated with testing of drugs for FDA approval for use in humans.

2. Background

Many biological functions are accomplished by altering the expression of various genes through transcriptional (e.g. through control of initiation, provision of RNA precursors, RNA processing, etc.) and/or translational control. For example, fundamental biological processes such as the cell cycle, cell differentiation and cell death, are often characterized by the variations in the expression levels of groups of genes.

Changes in gene expression also are associated with pathogenesis. For example, the lack of sufficient expression of functional tumor suppressor genes and/or the over expression of oncogene/proto-oncogenes could lead to tumorgenesis (Marshall, *Cell*, 64:313-326 (1991); Weinberg, *Science*, 254: 1138-1146 (1991)). Thus, changes in the expression levels of particular genes (e.g. oncogenes or tumor suppressors) serve as signposts for the presence and progression of various diseases.

Often drugs are screened and prescreened for the ability to interact with a major target without regard to other effects the drugs have on cells. Often such other effects cause toxicity in the whole animal, which prevent the development and use of the potential drug. Therefore, there is a need in the art to develop a systematic approach to test and develop new drugs for their effects on cellular metabolism without relying on gross morphologic and phenotypic effects.

Two approaches presently dominate the search for new drugs. The first begins with a screen for compounds that have a desired effect on a cell (e.g., induction of apoptosis), or organism (e.g., inhibition of angiogenesis) as measured in a specific biological assay. Compounds with the desired activity may then be modified to increase potency, stability, or other properties, and the modified compounds retested in the assay. Thus, a compound that acts as an inhibitor of angiogenesis when tested in a mouse tumor model may be identified, and structurally related compounds synthesized and tested in the same assay. A critical limitation of this approach is that, often, the mechanisms of action, such as the molecular target(s) and cellular pathway(s) affected by the compound, are unknown, and cannot be determined by the screen. Furthermore, this approach may provide little information about the specificity, either in terms of target or pathways, of the drug's effect. In contrast, the second approach to drug screening involves testing numerous compounds for a specific effect on a known molecular target, typically a cloned gene sequence of an isolated enzyme or protein. For example, high-throughput assays can be developed in which numerous compounds can be tested for the ability to change the level of transcription from a specific promoter or the binding of identified proteins.

The use of high-throughput screens is a powerful methodology for identifying drug candidates, however, it has its limitations. In particular, the assay provides little or no information about the effects of a compound at the cellular or organism level. In order to develop lead compounds into successful drugs, it is necessary not only to find compounds which are able to bind well to the primary target which is being screened, but also to ensure that the compounds are not simultaneously interacting with other targets within the cell. These effects must be tested by using the drug in a series of cell and whole animal studies to determine toxicity of side effects in vivo. In fact, analysis of the specificity and toxicity studies of candidate drugs can consume a significant fraction of the drug development process (see, e.g., Oliff et al., 1997, "Molecular Targets for Drug Development," in DeVita et al., Cancer: Principles & Practice of Oncology, $5^{TH}$ Ed., Lippincott-Raven Publishers, Philadelphia, Pa.).

Several gene expression assays are now becoming practicable for quantitating the drug effect on a large fraction of the genes and proteins in a cell culture (see, e.g., Schena et al., *Science*, 270:467-470; Lockhart et al., 1996, *Nature Biotechnology* 14:1675-1680; Blanchard et al., 1996, *Nature Biotechnology* 14:1649; Ashby et al., U.S. Pat. No. 5,569,588, issued Oct. 29, 1996). Raw data from these gene expression assays are often difficult to coherently interpret. Such measurement technologies typically return numerous genes with altered expression in response to a drug, typically 50-100, possibly up to 1,000 or as few as 10. In a typical case, without more analysis it is not possible to discern cause and effect from such data alone. The fact that one or a few genes among many has an altered expression in a pair of related biological states yields little or no insight into what caused this change and what the effects of this change are. These data in themselves do not inform an investigator about the pathways affected or primary targets of a drug. They do not indicate which effects result from effects on one primary target (e.g., the target screened in a high-throughput assay) versus which effects are the result of other primary targets of the drug.

Knowledge of all the primary targets is necessary in understanding efficacy, side-effects, toxicities, possible failures of efficacy, activation of metabolic responses, etc. Further, the identification of all primary targets of a drug can lead to discovery of alternative primary targets suitable to achieve the original therapeutic response. However, without effective methods of analysis, one is left to ad hoc further experimentation to interpret such gene expression results in terms of biological pathways and mechanisms. Systematic procedures for guiding the interpretation of such data and or such experimentation are needed.

Thus there is a need for improved (e.g., faster and less expensive) systems and methods to identify multiple primary targets of a drug, based on effective interpretation of such data as gene expression data.

SUMMARY OF THE INVENTION

The invention generally relates to compositions and methods for an effective and efficient new drug discovery, drug evaluation and drug toxicity. As discussed below, the invention has many important uses including the production of a gene and/or protein chips for identification of drug mediated gene and/or protein expression or repression. More particularly, the invention provides for a methods and compositions for construction of a biochip with multiple properties for use in identification of gene- and/or protein-induction or expression levels by drugs; allows for the evaluation of efficacy and toxicity of any drug of choice; prediction of efficacy and toxicity of newly-discovered drugs, families of drugs or classes of drugs. Experimental information acquired from the biochip is inputted into a Drug-Gene-Protein-Biology (DGPB) database from which experimental data can be mined and analyzed based on the users preferences.

The present invention provides a biochip array for evaluating the effect of a composition for the treatment of a disease. The biochip array comprises a surface having stably attached thereto a plurality of molecules capable of selective binding to at least one member of the group consisting of DNA, RNA, proteins, peptides or fragments thereof that is representative of an animal model for the disease. The member is provided from any metabolic pathway, apoptotic pathway, inflammatory pathway, cytokine production pathway, cellular growth product pathways, proto-oncogenes, oncogenes, antibodies or fragments thereof that are provided by the animal model.

The molecules used in the construction of the biochip array are derived from the "gold standard" animal model for human disease. The biochip array is preferably comprised of genes, nucleic acids, proteins, peptides or any fragments thereof derived from an animal model subjected to drug treatment. Either the whole animal or any organ or cell of the human disease animal model can be used to isolate the above molecules.

The "gold standard" human disease animal model can be any widely accepted animal which is representative of human disease. For example, the disease can be: allergy, arthritis, inflammatory disease, cancer such as breast cancer, testicular cancer, ovarian cancer and the like. One example of a "gold standard" animal model for allergy and asthma is the OVA-albumin induced mouse asthma model. One example of a "gold standard" animal model for arthritis is the collagen-induced arthritis mouse model. The disease also can be one which is caused by external environmental influences or stress-related diseases.

The invention also provides a method for predicting the effect of a test composition for the treatment of a disease, the method comprising selecting an animal model for the disease, providing a biochip array for evaluating the effect of said test composition for the treatment of the disease, said biochip array comprising a surface having stably attached thereto a plurality of molecules capable of selective binding to at least one member of the group consisting of DNA, RNA, proteins, peptides or fragments thereof that is representative of an animal model for the disease, using the test composition in the animal model to obtain a first set of biological markers representative of the effect of the test composition in the animal model, using the biochip array to generate a first set of data representative of the first set of biological markers, and evaluating the first set of data to predict the effect of the test composition on the disease. Preferably, the animal model is a standard animal model for human disease. The biological markers generally are selected from the group consisting of DNA, RNA, proteins, peptides or fragments thereof, wherein the markers are selected from any metabolic pathway; apoptotic pathway; inflammatory pathway; cytokine production pathway; cellular growth product pathways; proto-oncogenes; oncogenes; antibodies or fragments thereof provided by the animal model.

In preferred embodiments of the invention, further comprises selecting a second composition having a known treatment effect on the disease, using the second composition in the animal model to obtain a second set of biological markers representative of the effect of the second composition in the animal model, using the biochip array to generate a second set of data representative of the second set of biological markers, and comparing the first and second sets of data to predict the effect of the test composition on the disease.

In other preferred embodiments, the method further comprises generating a control set of biological markers representative of the effect of no treatment in the animal model, using the biochip array to generate a control set of data representative of the control set of biological markers, and comparing the first and control sets of data to predict the effect of the test composition on the disease.

The present invention also provides a method for predicting the effect of a test composition for the treatment of a disease comprising constructing a drug-gene-protein-biology database containing a plurality of data sets representative of the effects of a plurality of compositions in the animal model and comparing the test set of data with the database to predict the effect of the test composition on the disease.

In another embodiment the toxicity of a drug to humans can be evaluated prior to any human trials. The drug, for example can be an FDA-approved drug, a newly discovered drug, environmental toxic drug, or any environmental agent.

In another embodiment, the biochip is preferably used for drug discovery, evaluation of drug toxicity, predictability of toxic effects of a drug, identification of genes and proteins induced or repressed by the drug of action in a standard human disease animal model, or organs and cells thereof. The biochip is preferably comprised of genes, proteins, peptides or fragments thereof, combinations thereof, selected from any metabolic pathway; apoptotic pathway; inflammatory pathway; cytokine production pathway; cellular growth product pathways; proto-oncogenes; oncogenes; antibodies or fragments thereof.

In another embodiment, the biochip comprises gene fragments from any part of a gene or several parts of the same gene, whole genes, nucleic acids, proteins or fragments thereof, peptides or fragments thereof, from both treated and untreated whole animal human disease animal models, organs or cells.

In another embodiment, changes in gene expression between treated and untreated human disease animal models, or organs and cells thereof are detected by differentially labeling the nucleic acids and hybridizing sequence specific probes of choice. The sequence specific probe can be any sequence of any gene that is to be investigated.

In another embodiment, changes in protein expression between treated and untreated standard human disease animal models, or organs and cells thereof are detected by differentially labeling peptide probes and hybridizing sequence specific probes of choice. The sequence specific probe can be any sequence of any protein, peptide or fragment thereof, that is to be investigated.

In preferred embodiment the gene and protein expression changes in standard human disease animals that are treated with drug of choice versus the untreated are stored in a Drug-Gene-Protein-Biology database. The database is used to compare gene and protein expression profiles of standard human disease animal models treated with different drugs as compared to untreated animals. In one aspect, the database is used to evaluate a drug to be tested for therapeutic purposes, or to evaluate the molecular expression of efficacy of the drug for the designated therapeutic purpose, or to evaluate the molecular expression of toxicity of the drug.

In another preferred embodiment, the Drug-Gene-Protein-Biology database can be mined to predict gene and protein expression, the efficacy and potential toxicity of a drug belonging to a family or class of drugs.

In another embodiment the invention will include methods for the development of the Drug-Gene-Protein-Biology database. These methods will include systems, any novel software programs, devices and processes.

Other aspects of the invention are disclosed infra.

DETAILED DESCRIPTION OF THE INVENTION INCLUDING PREFERRED EMBODIMENTS THEREOF

Figure 1:
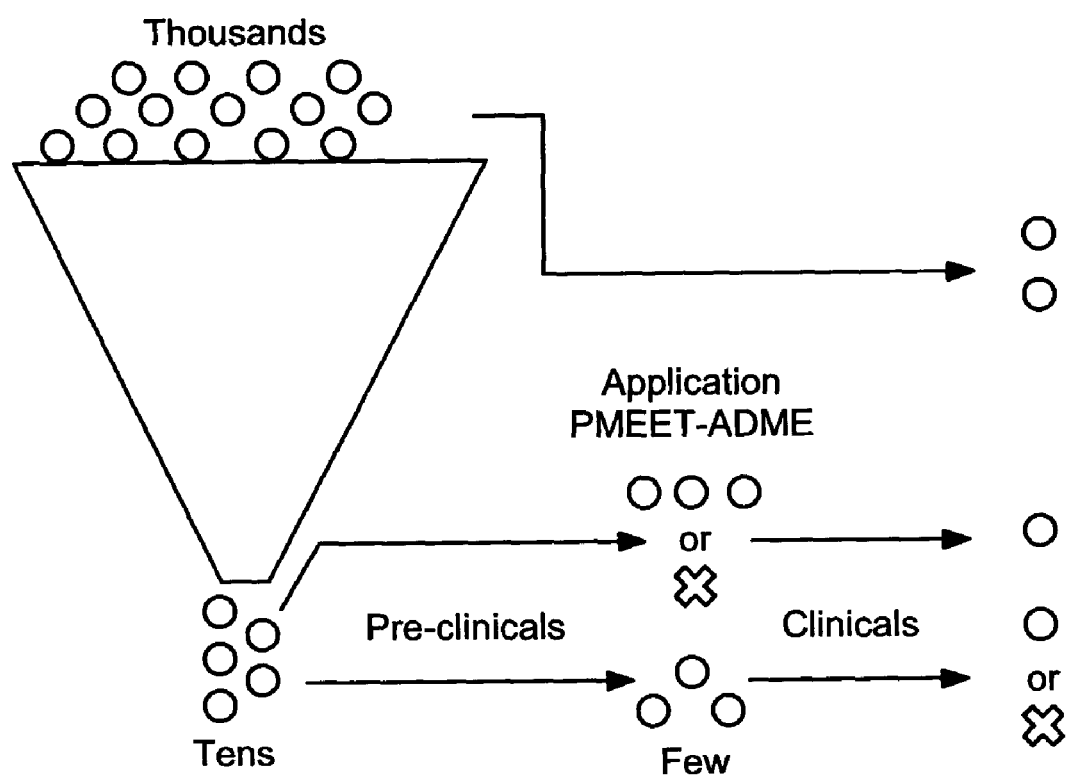
FIG. 1 is an illustration showing the application of the Predictive Molecular Expression of Efficacy, Toxicity, Adsorption, Distribution, Metabolism and Excretion (PMEET-ADME) process as applied to drug evaluation. The PMEET-ADME process can be applied to the drug evaluation at various points. One point is after drug selection during the pre-clinical evaluation process. Application of PMEET-ADME at this stage of the drug evaluation process provides a ranking of the candidate drug with regard to the benchmark drugs. The ranking reflects the projected efficacy, toxicity, adsorption, distribution, metabolism, and elimination of the candidate drug with respect to the benchmark drugs. A second point of application of the PMEET-ADME process is to drugs discarded during the drug selection process. In this case, drugs that were promising but did not survive the drug selection process are evaluated using PMEET-ADME process for any potential uses of the drug. This could result in previously discarded candidate drugs reaching FDA approval. A third point of application for the PMEET-ADME process is in the evaluation of drug-drug interactions and toxicity. Application of the PMEET-ADME process to drug-drug interactions during the pre-clinical phase of drug evaluation provides indications for possible adverse drug combinations prior to the treatment of humans.

The present invention provides for compositions and methods for construction of a biochip with multiple properties for use in identification of gene- and protein-induction by drugs; allows for the evaluation of efficacy and toxicity of any drug of choice; prediction of efficacy and toxicity of newly-discovered drugs, families of drugs or classes of drugs. The experimental information is inputted into a Drug-Gene-Protein-Biology (DGPB) database from which experimental data can be mined and analyzed based on the users preferences.

Whole genome gene expression profiling is a relatively new technique that allows the analysis of several thousands of gene fragments in one experiment. This technique is made possible by the attachment of several thousands of gene fragments, in assigned locations, to a glass slide or a silicon wafer to produce a "gene chip". A single gene chip can contain up to 40,000 gene fragments for gene expression analysis. Gene fragments can be from any part of a gene or several parts of the same gene. In general, the gene fragments are composed of two different groups, experimental and control. The experimental group contains fragments of genes whose expression is going to be profiled. While the control group contains the fragments of genes for several positive and several negative control genes. Control genes provide the means to monitor the quality of an experiment and provide "landmarks" for the location of the genes attached to the glass or silicon support. Typically the gene fragments are arranged in a grid pattern, repeated several times to form a "super grid" so as to allow multiple data points for analysis and landmarks to locate specific gene fragments (Microarray Biochip Technology, ed. Mark Schena (Natick, Mass.: Eaton Publishing 2000).

The gene chip can be used to evaluate the differences in gene expression between untreated and treated cells. This is accomplished by differentially labeling the nucleic acids derived from the treated and untreated cells followed by sequence specific hybridization of the differentially labeled nucleic acids to the same gene chip. Conclusions and comparisons about the genes differentially expressed between the treated and untreated samples can be made after removal of the excess differentially labeled nucleic acid from the gene chip, data collection and data analysis (Microarray Biochip Technology, ed. Mark Schena (Natick, Mass.: Eaton Publishing 2000; Duggan, D. J., Bittner, M., Chen, Y., Meltzer, P. and Trent, J. M. (1999). Expression profiling using cDNA microarrays. *Nature Genetics* Vol. 21S, p. 10-14)).

Genes that are affected by the treatment of the cells are determined by comparing and identifying the differential gene expression between untreated and treated cells. For example, gene fragments having proportionally less labeled nucleic acid from the treated cells than from the untreated cells are said to have decreased expression or to have "repressed" gene expression. Whereas gene fragments that have proportionally more labeled nucleic acid from the treated cells than from the untreated cells are said to have increased expression or to have "induced" gene expression.

Analysis of a list containing the gene fragments, level of induction or repression or no change, and the function of the gene allows the identification of biological pathways that have altered gene expression patterns. Thus, the massive amount of genetic information provided by a single gene chip experiment allows the identification of biochemical pathways exhibiting altered gene expression patterns due to a specific drug treatment. A gene chip provides information about altered gene expression patterns from which the expression patterns of induction or repression of proteins can be deduced but, with the additional information provided by a "protein chip" the actual expression pattern of the proteins can be deduced and correlated with gene expression.

Subjecting human disease animal models to a battery of different drug treatments results in the induction or repression of many pathways at the cellular level, for example, gene and protein expression or repression. The present invention comprises the use of gene and protein chips for identifying these changes and use of the information obtained from the gene and/or protein biochip to build a Drug-Gene-Protein-Biology Database. Experimental treatments that are limited to a family of drugs identifies genes and proteins induced and repressed by the individual drugs and the drug family. Combining the gene expression profile and protein expression profile information from individual drugs, a drug family or a class of drugs into a single "Drug-Gene-Protein-Biology" database (DGPB) provides for the identification of genes and proteins that respond to individual drugs as well as drug families and classes. Furthermore, in preferred embodiments, the DGPB database will include information from metabolic profiling and the typical industrial methods of evaluating a drug, drug family or drug class effect on the treated biological material. These last two profiling methods, the metabolic and the typical industrial, has the added advantage of providing a link between the present methods of drug evaluation and the future methods of drug evaluation.

In the present invention, the Drug-Gene-Protein-Biology (DGPB) database links drug action, genetic response, protein response and biological response together providing information storage so that software tools can compare and analyze data. Such software tools are well known to those skilled in the art. As the information in the database expands, the capacity of the database provides for a continuing increase in the ability to use the information for purposes of predicting the biological response of a new drug based on the genes and proteins that demonstrate induction or repression. Additionally, the database can be "mined" for the identification of new drug targets, new biological switches, new biological pathways, and the actions of drugs and drug treatments across a wide gene and protein profile.

Experiments conducted to evaluate a drug for its molecular (both at the genetic and amino acid level) expression, efficacy, toxicity, ability to be adsorbed, will be referred to as Predictive Molecular Expression of Efficacy, Toxicity, Adsorption, Distribution, Metabolism and Excretion (PMEET-ADME) experiments. These experiments are conducted in accord with the present invention using biochips discussed infra. Information obtained from such experiments are inputted into the DGPB database, which will provide information predictive of a new drug's success in FDA clinical trials.

A PMEET-ADME experiment has many advantages over typical or presently performed gene chip based experiments. For example, animal models that are medically relevant models of human diseases (pre-clinical animal models) for the drug are used in the evaluation. These models include use of transgenic mice and other transgenic animals including p53 tumor suppressor gene knockouts for tumorigenic studies, use of a transgenic model for impaired glucose tolerance and human Alzheimer's amyloid precursor protein models for the study of glucose metabolism and for the pathogenesis of Alzheimer's disease, respectively, etc. The biochips of the present invention are used for analysis of both genes and proteins so that genes and proteins induced or repressed by the drugs can be identified. Either the whole animal, or key organs such as lymph node, brain, kidney, liver, etc., are used to isolate genes and proteins for construction of the biochips. The other major advantage of the biochips is that they are also used in determining the metabolic profile and potential toxicity of a new drug or identify new uses for drugs that have not been approved by the FDA to treat a certain condition. More importantly, the experimental information obtained from the biochip of the present invention is used for correlating the gene and protein profile of known toxic drugs with the profile of newly discovered drugs, thereby providing a predictive model of drug toxicity for either individual drugs, families of drugs, sub-classes of drugs, etc. The advantage is that these toxic drugs are identified prior to proceeding to further experimental or clinical trials, thereby, cutting the cost of drug production.

The other major advantage of the present experiment is that it provides for a database that is used for the organization of data, analysis of data, and mining of data. In this way a predictive index can be determined for the possibility of a new drug succeeding in FDA trials.

The combination of the Predictive Molecular Expression of Efficacy, Toxicity, Adsorption, Distribution, Metabolism and Excretion (PMEET-ADME) experiments and the DGPB database as applied in the present invention for drug evaluation will improve the efficiency of drug evaluation, provide a predictive method for evaluation of a drug and provide evaluation of a drug in diseased or stressed animals. These advances in drug evaluation will have the benefit of providing drug evaluations in whole animal models that are medically relevant models of human diseases, animals that stressed due to the disease, and drug evaluations that are compared against currently used drugs.

The PMEET-ADME process preferably is applied to the drug evaluation process at one of the following three locations (FIG. 1). The first location is after drug selection during the pre-clinical evaluation process. Application of PMEET-ADME at this stage of the drug evaluation process provides a ranking of the candidate drugs with regard to benchmark drugs in medically relevant animal models of human disease of interest. The ranking reflects the projected efficacy, toxicity, adsorption, distribution, metabolism and elimination of the candidate drug with respect to benchmark drugs. A second site of application is to the drugs that have been discarded during the drug selection process. In this case, drugs that showed promise, but were not selected to continue through the selection process are evaluated using the PMEET-ADME process for determining the probability of the drugs achieving FDA approval. A third location for the application of the PMEET-ADME process is in the evaluation of drug-drug interactions and toxicity. Application of the PMEET-ADME process to drug-drug interactions during the pre-clinical phase of drug evaluation provides indications for possible adverse drug combinations prior to the treatment of humans.

Figure 2:
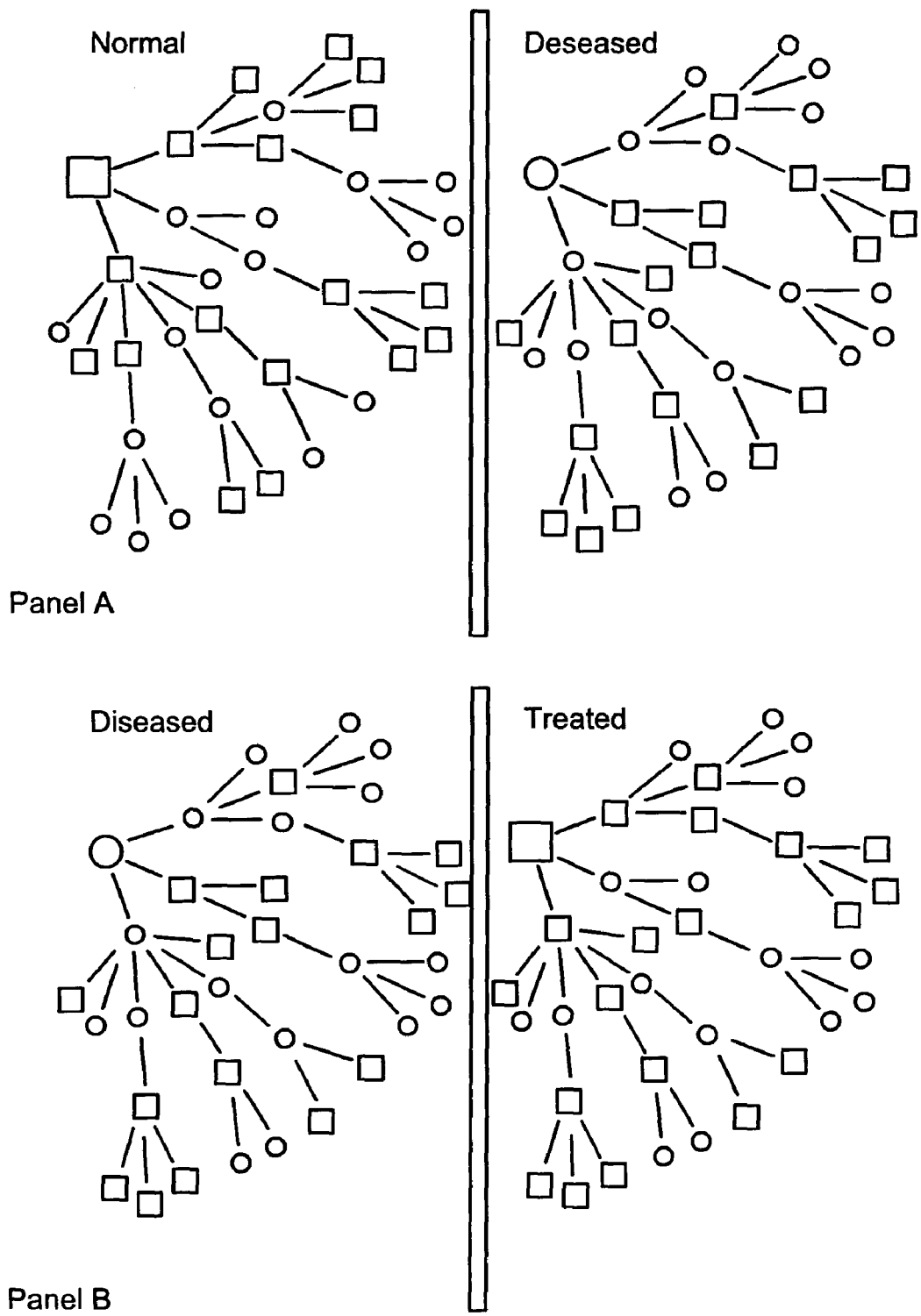
FIG. 2 is a diagram showing the identification of gene and protein expression networks. Panel A is a diagram of a normal and diseased state gene or protein expression network. Panel B is a diagram of the diseased and treated state gene or protein expression network. In both panels a square indicates a down regulation of a gene or protein and a circle indicates an up regulation of a gene or protein.

The identification and elucidation of biological pathways involved in the disease process, disease progression, secondary effects of a disease as well as the response of the disease and the animal to treatment by drugs provides a novel process for the evaluation of candidate drugs, as illustrated in FIG. 2. The use of gene and protein biochips to analyze medically relevant animal models for human disease provides for the identification of biological pathways that are specifically involved in the biology of a disease. The rationale is that since these medically relevant models of human disease have been previously used to study human disease and to evaluate treatments for a disease, data obtained from these animal models is used to extrapolate gene and protein expression data to the human disease. For example, gene and protein expression of biological pathways involved in the disease, disease treatment, disease toxicology efficacy of a treatment as well as the identification of drugs having toxic effects. A model for evaluating a disease and treatment process can be constructed by understanding the expression and modification of these key genes and proteins.

These models require the identification of the key genes and proteins and in the case of the genes the expression status (induced or repressed) and in the case of the proteins the expression and modification status (induced or repressed as well as modification event). The identified individual key gene or protein events are assigned a weighting factor based on their response to the benchmarking drugs. Thus, by constructing biochips containing the key genes and proteins an evaluation of a candidate drug against benchmark drugs can be performed.

The term "biochip" as used herein, is a microarray chip comprised of gene fragments from any part of a gene or several parts of the same gene, whole genes, nucleic acids, proteins or fragments thereof, peptides or fragments thereof. The biochip can be comprised of any combinations of the above molecules in any pattern on the chip.

The term "pattern" as used herein, can be parallel horizontal or vertical lines, spots, circles, grids, checkered designs, or any other desired design.

Examples of Gold Standard Animal Models

The terms, "gold standard animal models", "medically relevant animal model", or "animal model" are used interchangeably throughout the disclosure. As used herein, the above terms refer to any animal model that has been used to study a human disease, including any standard, well-accepted animal models of various human disease indications, or animal models that have been used to study the effects of therapies and drugs for pre-clinical evaluation. These animal models also include transgenic animals.

Transgenic Animals as Gold Standard Human Disease Animal Models

Transgenic animals are widely available, for example, transgenic mice which constitutively express an antibody-type molecule encoded by the transgene and which has an IgE heavy chain constant region and is specific for a pre-defined antigen, provide an allergic reaction to that antigen without prior sensitization and are useful as allergy models.

The term "animal" is used herein to include all vertebrate animals, except humans. It also includes an individual animal in all stages of development, including embryonic and fetal stages.

A "transgenic animal", as used herein, is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA.

The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals. The genetic alteration or genetic information may be foreign to the species of animal to which the recipient belongs, or foreign only to the particular individual recipient. In the last case, the altered or introduced gene may be expressed differently than the native gene.

Construction of transgenic animals is well-known in the art. A type of target cell for transgene introduction is the embryonal stem cell (ES). ES cells may be obtained from pre-implantation embryos cultured in vitro and fused with embryos (M. J. Evans et al., *Nature* 292: 154-156 (1981); Bradley et al., *Nature* 309: 255-258 (1984); Gossler et al. *Proc. Natl. Acad. Sci.* USA 83: 9065-9069 (1986); and Robertson et al., *Nature* 322, 445-448 (1986)). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, *Science* 240: 1468-1474 (1988)).

To determine the contributions of individual genes and their expression products isolated genes to selectively inactivate the native wild-type gene in totipotent ES cells are used and then generate transgenic mice. The use of gene-targeted ES cells in the generation of gene-targeted transgenic mice was described 1987 (Thomas et al., *Cell* 51:503-512, (1987)) and is reviewed elsewhere (Frohman et al., *Cell* 56:145-147 (1989); Capecchi, *Trends in Genet.* 5:70-76 (1989); Baribault et al., *Mol. Biol. Med.* 6:481-492, (1989); Wagner, *EMBO J.* 9: 3025-3032 (1990); Bradley et al., *BioTechnology* 10: 534-539 (1992)).

Techniques are available to inactivate or alter any genetic region to any mutation desired by using targeted homologous recombination to insert specific changes into chromosomal alleles. However, in comparison with homologous extrachromosomal recombination, which occurs at frequencies approaching 100% homologous plasmid-chromosome recombination was originally reported to only be detected at frequencies between $10^{-6}$ and $10^{-3}$ (Lin et al., *Proc. Natl. Acad. Sci.* USA 82:1391-1395 (1985); Smithies et al., *Nature* 317: 230-234 (1985); Thomas et al., *Cell* 44:419-428, (1986); Song et al., *Proc. Natl. Acad Sci.* USA 84:6820-6824 (1987)). Nonhomologous plasmid-chromosome interactions are more frequent, occurring at levels $10^5$-fold (Lin et al., *Proc. Natl. Acad Sci.* USA 82:1391-1395 (1985)) to $10^2$-fold (Thomas et al., *Cell* 44:419-428 (1986); Song et al., *Proc. Natl. Acad. Sci.* USA 84:6820-6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., *Nucleic Acids Res.* 16:8887-8903 (1988); Kim et al, *Gene* 103:227-233 (1991)). Alternatively, a positive genetic selection approach has been developed in which a marker gene is constructed which will only be active if homologous insertion occurs, allowing these recombinants to be selected directly (Sedivy et al., *Proc. Natl. Acad. Sci.* USA 86:227-231 (1989)). One of the most general approaches developed for selecting homologous recombinants is the positive-negative selection (PNS) method developed for genes for which no direct selection of the alteration exists (Mansour et al., *Nature* 336:348-352: (1988); Capecchi, *Science* 244:1288-1292, (1989); Capecchi, *Trends in Genet.* 5:70-76 (1989)). The PNS method is more efficient for targeting genes that are not expressed at high levels because the marker gene has its own promoter. Nonhomologous recombinants are selected against by using the Herpes Simplex virus thymidine kinase (HSV-TK) gene and selecting against its nonhomologous insertion with the herpes drugs such as gancyclovir (GANC) or FIAU (1-(2-deoxy 2-fluoro-B-D-arabinofuranosyl)-5-iodouracil). By this counter-selection, the number of homologous recombinants in the surviving transformants can be enriched.

As used herein, a "targeted gene" or "Knock-out" (KO) is a DNA sequence introduced into the germline of a non-human animal by way of human intervention, including but not limited to, the above described methods. The targeted genes of the invention include DNA sequences that are designed to specifically alter cognate endogenous alleles.

The methods for evaluating the targeted recombination events as well as the resulting knockout mice are readily available and known in the art. Such methods include, but are not limited to DNA (Southern) hybridization to detect the targeted allele, polymerase chain reaction (PCR), polyacrylamide gel electrophoresis (PAGE) and Western blots to detect DNA, RNA and protein.

The OVA-Induced Bronchial Asthma Mouse Model for Inhibition of Mast Cell Degranulation Asthma is a complex disease, which is characterized by spontaneous exacerbation of airways obstruction and persistent bronchial hyperresponsiveness. Chronic infiltration with activated T-lymphocytes, eosinophils and macrophages/monocytes of the airway submucosa is another established feature. Inflammatory mechanisms, with expression of cytokines, and the release of inflammatory mediators, underlie the pathogenesis of bronchoconstriction and bronchial hyperresponsiveness. However, much of the pathogenic mechanism remains unclear, e.g., the mechanisms that induce persistence of symptoms and chronic inflammation and the interventions necessary to control and prevent the disease.

It has long been recognized that a single inhaled allergen challenge can induce an acute increase in airway responsiveness in some individuals and animal models. However, repeated allergen inhalations have demonstrated more pronounced, consistent, and prolonged increases in airway responsiveness. This mouse model of long-term repeated inhalations of allergen has been used to study the long term effect of allergic diseases in the lung, and to delineate the cells, mechanisms, molecules, and mediators involved in the induction of airway hyperresponsiveness of lung in humans.

Some common examples of inflammatory diseases are asthma, lupus, multiple sclerosis, osteoarthritis, psoriasis, Crohn's disease and rheumatoid arthritis.

According to the invention different drugs may be used to modulate the expression of genes involved in inflammatory diseases. Tables 1 through 4 lists a number of genes and/or proteins that may be modulated by different drugs; table 1 (CD markers), table 2 (adhesion molecules) table 3 (chemokines and chemokine receptors), and table 4 (interleukins and their receptors). Also included as particularly interesting are the genes encoding the immunoglobulin E (IgE) and the IgE-receptor (FcεRIα) as well as the genes for the other immunoglobulins, $IgG_{1-4}$, $IgA_1$, $IgA_2$, IgM, IgE, and IgD encoding free and membrane bound immunoglobulins and the genes encoding their corresponding receptors.

TABLE 1

CD markers

| | | | | |
|---|---|---|---|---|
| CD1a-d | CD30 | CD61 | CD91 | CD121 |
| CD2 | CD31 | CD62E | CDw92 | CD122 |
| CD3 | CD32 | CD62L | CD93 | CDw123 |
| CD4 | CD33 | CD62P | CD94 | CD124 |
| CD5 | CD34 | CD63 | CD95 | CDw125 |
| CD6 | CD35 | CD64 | CD96 | CD126 |
| CD7 | CD36 | CD65 | CD97 | CD127 |
| CD8 | CD37 | CD66a-e | CD98 | CDw128 |
| CD9 | CD38 | CD67 | CD99 | CD129 |
| CD10 | CD39 | CD68 | CD100 | CD130 |
| CD11a | CD40 | CD69 | CD101 | CDw131 |
| CD11b | CD41 | CD70 | CD102 | CD132 |
| CD11c | CD42a-d | CD71 | CD103 | CD133 |
| CDw12 | CD43 | CD72 | CD104 | CD134 |
| CD13 | CD44 | CD73 | CD105 | |
| CD14 | CD45 | CD74 | CD106 | |
| CD15 | CD46 | CDw75 | CD107a,b | |
| CD16 | CD47 | CDw76 | CDw08 | |
| CDw17 | CD48 | CD77 | CD109 | |
| CD18 | CD49a-f | CDw78 | CD110 | |
| CD19 | CD50 | CD79a,b | CD111 | |
| CD20 | CD51 | CD80 | CD112 | |
| CD21 | CD52 | CD81 | CD113 | |
| CD22 | CD53 | CD82 | CD114 | |
| CD23 | CD54 | CD83 | CD115 | |
| CD24 | CD55 | CDw84 | CD116 | |
| CD25 | CD56 | CD85 | CD117 | |
| CD26 | CD57 | CD86 | CD118 | |
| CD27 | CD58 | CD87 | CD119 | |
| CD28 | CD59 | CD88 | CD120a,b | |
| CD29 | CDw60 | CD89 | | |
| CD30 | | CD90 | | |

TABLE 2

Adhesion molecules

| | | | | |
|---|---|---|---|---|
| L-selectin | TCRγ/δ | BB-1 | Integrin α7 | Integrin α6 |
| P-selectin | CD28 | N-cadherin | Integrin α8 | Integrin β5 |
| E-selectin | LFA-3 | E-cadherin | integrin αV | Integrin αV |
| HNK-1 | PECAM-1 | P-cadherin | Integrin β2 | Integrin β6 |
| Sialyl-Lewis X | VCAM-1 | Integrin β1 | integrin αL | Integrin αV |
| CD15 | ICAM-2 | Integrin α1 | Integrin αM | Integrin β7 |
| LFA-2 | ICAM-3 | Integrin α2 | Integrin αX | Integrin αIEL |
| CD22 | Leukosialin | Integrin α3 | Integrin β3 | Integrin α4 |
| ICAM-1 | HCAM | Integrin α4 | Integrin αV | Integrin β8 |
| N-CAM | CD45RO | Integrin α5 | Integrin αIib | Integrin αV |
| Ng-CAM | CD5 | Integrin α6 | Integrin β4 | |
| TCRα/β | HPCA-2 | | | |

TABLE 3

Chemokines and Chemokine receptors

| C—X—C chemokines | C—C chemokines | C chemokines | | hemokine eceptors |
|---|---|---|---|---|
| IL-8 | MCAF/MCP-1 | ABCD-1 | Lymphotactin | CCR1 |
| NAP-2 | MIP-1 α,β | LMC | | CCR2 |
| GRO/MGSA | RANTES | AMAC-1 | | CCR3 |
| γIP-10 | I-309 | NCC-4 | | CCR4 |
| ENA-78 | CCF18 | LKN-1 | | CCR5 |
| SDF-1 | SLC | STCP-1 | | CCR6 |
| 1-TAC | TARC | TECK | | CCR7 |
| LIX | PARC | EST | | CCR8 |
| SCYB9 | LARC | MDC | | CXCR1 |
| B cell-attracting chemokine 1 | EBI 1 | Eotaxin | | CXCR2 |
| | HCC-1 | | | CXCR3 |
| | HCC-4 | | | CXCR4 |
| | | | | CXCR5 |
| | | | | $CX_3CR$ |

TABLE 4

Interleukins and their receptors

| | | | | |
|---|---|---|---|---|
| G-CSF | IL-2 Rα | IL-8 | IL-16 | TGF-β1 |
| G-CSF R | IL-2 Rβ | IL-9 | IL-17 | TGF-β1,2 |
| GM-CSF | IL-2 Rγ | 1L-9 R | IL-18 | TGF-β2 |
| IFN-γ | IL-3 | IL-10 | PDGF | TGF-β3 |
| IGF-I | IL-3 Rα | IL-10 R | PDGF A Chain | TGF-β5 |
| IGF-I R | IL-4 | IL-11 | PDGF-AA | LAP TGF-β1 |
| IGF-II | IL-4 R | IL-11 R | PDGF-AB | Latent TGF-β1 |
| IL-1α | IL-5 | IL-12 | PDGF B Chain | TGF-βbpl |
| IL-1β | IL-5 Rα | IL-12 p40 | PDGF-BB | TGF-βRII |
| IL-1 RI | IL-6 | IL-12 p70 | PDGF Rα | TGF-βRIII |
| IL-1 RII | IL-6 R | IL-13 | PDGF Rβ | |
| IL-1ra | IL-7 | IL-13 Rα | TGF-α | |
| IL-2 | IL-7 R | IL-15 | TGF-β | |

It should be appreciated that in the above tables 1 through 4, an indicated gene means the gene and all currently known variants thereof, including the different mRNA transcripts to which the gene and its variants can give rise, and any further gene variants which may be elucidated. In general, however, such variants will have significant homology (sequence identity) to a sequence of a table above, e.g. a variant will have at least about 70 percent homology (sequence identity) to a sequence of the above tables 1-4, more typically at least about 75, 80, 85, 90, 95, 97, 98 or 99 homology (sequence identity) to a sequence of the above tables 1-4. Homology of a variant can be determined by any of a number of standard techniques such as a BLAST program.

Sequences for the genes listed in Tables 1-4 can be found in GENBANK™, a nucleotide and protein sequence database maintained by the National Center for Biotechnology Information (NCBI). The gene sequences may be genomic, cDNA or mRNA sequences. Preferred sequences are mammalian genes containing the complete coding region and 5' untranslated sequences. Particularly preferred are human cDNA sequences.

Induced Type II Collagen Arthritis Mouse Model

A mouse model is used to evaluate the effect of the compounds in accord with the present invention on the histological, radiographic and clinical appearance of induced type II collagen arthritis.

Autoimmune diseases cause significant and chronic morbidity and disability. Arthritis in its many forms is representative of a family of autoimmune diseases. In the clinical realm, rheumatoid arthritis (RA) is the most common form of the severe arthrodysplastic disease. All clinicians agree that RA is a progressive disease.

The histopathology of arthritic lesions occurring in murine collagen induced arthritis model (CIA) share enormous similarities to that of RA in human patients. Thus, murine CIA is an accepted model to study potential therapeutic treatments of RA.

Any acceptable animal model can be used for testing gene expression induced by drugs. Other examples of gold standard animal models of human disease include the following.

The animal model for Alzheimer's disease in humans, which is produced by placing a selective lesion in a subcortical nucleus (nucleus basalis of Meynert) with a resultant cortical cholinergic deficiency, similar in magnitude to that seen in early to moderate stage Alzheimer's disease. Numerous behavioral deficits, including the inability to learn and retain new information, characterizes this lesion. Drugs that can normalize these abnormalities would have a reasonable expectation of efficacy in Alzheimer's disease. Haroutunian, V., Kanof, P., Davis, K. L: Pharmacological Alleviations of Cholinergic-Lesion-Induced Memory Defects in Rats. *Life Sciences*, 37:945-952 (1985).

The OVCAR3 human ovarian cancer animal model accurately approximates the clinical presentation of stage M-IV ovarian cancer of peritoneal carcinomatosis. Untreated, OVCAR3 tumor is lethal to nude mice.

Animal Models for Evaluating Suspected Environmentally Influenced Carcinogenicity The biochip chip can also be used to determine carcinogenicity or toxicity of various environmental agents by comparing the gene expression between animals exposed to the agent versus those animals not exposed. In order to determine carcinogenicity of suspected environmental influences, the cancer suppressing gene of an animal model is controlled by genetic manipulation to render it susceptible to carcinogenic influences. In this regard, one of a pair of cancer suppressing genes of the animal is rendered inactive, so that the offspring of the animal may be exposed to the expected environmental carcinogen for testing purposes. Tumor development of the animal thus exposed is a positive indication of carcinogenicity of the suspected environmental influence.

As an example of production of a mouse model for evaluation of carcinogenicity of suspected environmental influences, a strain of mice had been developed having heterogeneity of the RB gene. Exposure of the mouse to a carcinogen results in alteration of the dominant RB gene thereby resulting in production of the homozygous, recessive condition with attendant tumor development. (See, for example, *Nature*, 326:292, (1987); *Nature*, 326:295, (1987); *Proc. Natl. Acad Sci*. U.S.A., 83:9065, (1986)).

Immunization of Animal Models

To determine whether a drug induces or represses a gene or protein for design of drug treatments, animal models can also be immunized with an antigen of choice such as allergens, inflammatory proteins or peptides, haptens and the like. For example, in the OVA animal model, the animals are immunized with allergens and then the drug of choice is administered to determine any changes in gene or protein expression. Immunization of animals is well known in the art. The antigen can be administered to the mammal by any number of suitable routes such as subcutaneous, intraperitoneal, intravenous, intramuscular, intracutaneous injection, topically or orally. The optimal immunizing interval, immunizing dose, etc., can vary within relatively wide ranges. Typical procedures involve injection of the antigen several times over a number of months. Antigen may be co-administered with an adjuvant to increase the antigenicity of the antigen. For example, in the CIA mouse model of arthritis, lipopolysaccharide (LPS) can be used as an adjuvant to increase the antigenicity response to collagen in inducing a particularly aggressive form of arthritis in the mouse.

Identification of Pathways that can be Influenced by Drugs

Treatment of animals with the drug of choice will influence expression or repression of certain proteins, for example, those proteins involved in inflammation if the drug of choice is anti-inflammatory; biological pathways, for example, enzymatic pathways, regulatory pathways, chemokine pathways, etc. The drug of choice may repress or allow overexpression of a particular protein in a pathway. For example, many cellular pathways are stimulated via the G-protein, using phospholipases as secondary messengers. Three phospholipases have been characterized and can be used in the design of the biochip to determine activation of, for example, inflammatory pathways. Other phospholipases can be included when they are characterized sufficiently.

One is phospholipase C, $PLC_{\beta 2}$, which generates two second messengers, 1,4,5-inositol triphosphate ($IP_3$) and diacylglycerol (DG). The $\beta$, $\gamma$ subunits of the G-protein generated during activation of the FPR [formyl peptide receptor] activate $PLC_{\beta 2}$. $IP_3$ binds to certain calcium channels to stimulate the release of calcium from intracellular storage, resulting in an increase in the cytosolic concentration of calcium that is observed during stimulation by chemoattractants. DG, in concert with released calcium, activates protein kinase C (PKC).

A second, phospholipase $A_2$ ($PLA_2$), generates arachidonic acid from the phospholipids of the inner face of the plasma membrane. Arachidonic acid provides the precursors for the inflammatory mediators such as leukotrienes and prostaglandins. $PLA_2$ is activated upon phosphorylation by the mitogen-activated protein (MAP) kinase.

A third phospholipase is phospholipase D (PLD), which generates phosphatidic acid and choline from phosphatidylcholine. Phosphatidic acid may be involved in activation of respiratory burst oxidase in addition to playing a role in the production of DG, which activates PKC. However, activation of PLD requires calcium. For example, FMLP (fMet-Leu-Phe) cannot stimulate PLD in calcium-depleted cells (Kessels et al., *J. Biol. Chem*. 266: 23152-23156, 1991). In addition, it appears that the G-protein Arf and G-protein Rho regulate PLD activity (Brown et al., *Cell* 75: 1137-1144, 1993; Cockcroft et al., *Science* 263: 523-526, 1994; Singer et al., *J. Biol. Chem*. 270: 14944-14950, 1995).

As discussed above, PKC is activated by DG, which is generated by PLC. PKC acts to phosphorylate serine and threonine residues. PKC consists of six different isoforms, three of which are sensitive to intracellular calcium ($\alpha$, $\beta$, and $\gamma$ forms) and three that are not ($\delta$, $\epsilon$, and $\zeta$ forms). Neutrophils contain the $\alpha$, $\beta$, and $\zeta$ forms but not the $\gamma$ form. The calcium-dependent and DG-dependent PKC (PKC-$\beta$) responds to FMLP and phorbol ester stimulation by translocating from the cytosol to the membrane. It then phosphorylates a number of cytosolic proteins, such as those involved in the respiratory burst oxidase system. FMLP can also activate the calcium-independent, DG-dependent and phosphatidyl serine-dependent PKC form. Thus, a drug of choice which acts in a similar manner may be identified or its mechanism of action elucidated allowing for design of new drugs with lower side effects.

The MAP kinase reportedly is activated by the β, γ subunits of the G-proteins by the activities of Ras and Raf. This kinase pathway is also stimulated by $C_{5a}$ and IL-8 (Buhl et al., *J. Biol. Chem.* 270: 19828-19832, 1995; Knall et al., *J. Biol. Chem.* 271: 2832-2838, 1996). MAP kinase induces tyrosine phosphorylation of several regulatory proteins, such as the extracellular signal-regulated kinase (ERK)-1. Thus MAP, or regulatory proteins such as (ERK-1) in the pathway can be used in the design of the biochip.

Phosphatidylinositol 3-kinase (PI3K) is responsible for the formation of PI triphosphate ($PIP_3$) that is observed upon stimulation by FMLP.

The above is just one example of how a drug may affect a certain pathway by repressing or inducing expression of one protein, for example G-protein.

Any gene or protein involved in such pathways can be used in the design of the biochip in order to elucidate at which stages drugs repress, express or do not change expression levels. Examples of genes and/or proteins in pathways that can be influenced by drugs for use in designing the protein and/or gene chips are listed in Table 5.

TABLE 5

| Gene Name | Gene Abbreviation | Comments |
|---|---|---|
| | BMP-2 | |
| | Caspase 1 | |
| | CD 4 | |
| | CD 11 | |
| | FAS antigen | |
| | G-CSF | |
| | GM-CSF | |
| | ICAM-1 | |
| | IFN α4 | |
| | IgER | |
| | IgE | |
| | IL 1 | |
| | IL 3 | |
| | IL 4 | |
| | IL 5 | |
| | IL 10 | |
| | IL 13 | |
| | IL 15 | |
| | MCSF | |
| | MLP-1 | |
| | RANTES | |
| | TGFα | |
| | TNFα | |
| | TNFβ | |
| | C5a | |
| | IL8 | |
| | IFNα | |
| | ICAM | |
| | IL2 | |
| | IL6 | |
| Formal Peptide Receptor | FPR | |
| | VCAM | |
| Nitrous Oxide | | Pathway |
| Oxide | | Pathway |
| Peroxide | | Pathway |
| Carbonic Acid | | Pathway |
| Histamine Release | | Pathway |
| Matrix Metalloproteinases | MMPs | Pathway |
| Tissue Inhibitors of MMPs | TIMPs | Pathway |
| G-proteins | | Pathway(s) |
| Peripheral Blood Cellular controls | | Pathway |
| Mucus Production | | Pathway |
| Eosinophil Activation and Mobilization | | Pathway |
| | P13 | |
| | Raf | |
| | Ras | |
| | Pp60 Src | |
| | ERK-1 | |
| G protein α | | |
| G protein β | | |
| G-protein γ | | |
| | PLC γ | |
| | Grb2 | |
| | SOS | |
| | Shc | |
| | MAP K | |
| Jun Kinase | | |
| | Myc | |
| | Fos | |
| | NFK B | |
| | IKB | |
| Apoptosis | | Pathway |
| | PLC β | |
| | Syk | |
| | JAK 3 | |
| | FCεR1 | |
| Collagen | | Pathway |
| Lamin | | Pathway |
| Receptors | | Cell Proliferation |
| Transcription Factors | | Cell Proliferation |
| Growth Factors | | Cell Proliferation |
| Connexins | | Cell Proliferation |
| Phosphatases | | Cell Proliferation |
| Kinases | | Cell Proliferation |
| Helicases | | DNA Damage and Repair |
| DNA repair genes | | DNA Damage and Repair |
| | GADDS | DNA Damage and Repair |
| Topoisomerases | | DNA Damage and Repair |
| | Eras | DNA Damage and Repair |
| Serum Amyloids | | Inflammation |
| Chemokines | | Inflammation |
| Interleukins | | Inflammation |
| Adhesion Molecules | | Inflammation |
| Glutathione Enzymes | | Metabolism |
| P450 | | Metabolism |
| Methyltransferases | | Metabolism |
| Redox Enzymes | | Metabolism |
| Glucuronidation Enzymes | | Metabolism |
| Oxide Response Genes | | Oxidative stress |
| Superoxide Dismutase | SOD | Metabolism |
| Peroxisomal Enzymes | | |
| Caspase | | Apoptosis |
| | Fas | Apoptosis |
| | Bak | Apoptosis |
| Calcineurin | | Apoptosis |
| Cyclins | | Apoptosis |
| | Bax | Apoptosis |
| | TNFs | Apoptosis |
| | MDR | Transport |
| Organic Anion | | Transport |
| Cationic Anion | | Transport |
| | P53 | |
| | MDM2 | |
| | HIF1 | |

PMEET-ADME Biochip

One skilled in the art will appreciate that an enormous number of array designs are suitable for the practice of this invention. The biochip can be comprised of any molecule, for example, oligonucleotides, DNA, PNA (peptide nucleic acids) or RNA, proteins, peptides, amino acid sequences or fragments thereof.

Preferably, the oligonucleotides that comprise the biochip are of a defined length and similarity. This allows for similar hybridization characteristics. For the hybridization characteristics to be similar across a wide range of oligonucleotides, as is well known to those skilled in the art, it is required that the oligonucleotides be of the substantially same length, have a similar percentage of Guanine to Cytosine content and lack any extensive runs of poly A, poly G, poly C, or poly T tracts. The goal of having these parameters is to produce oligonucleotides that have similar melting and hybridization temperatures. Additionally, these oligonucleotides should, preferably, lack lengthy complementary regions and not form hairpins.

One method for generating the biochip of the present invention is disclosed in U.S. Pat. No. 6,093,302, by Montgomery. The method disclosed is a solid phase synthesis method for the preparation of diverse sequences of separate polymers or nucleic acid sequences using electrochemical placement of monomers or nucleic acids at a specific location on a substrate containing at least one electrode that is preferably in contact with a buffering or scavenging solution to prevent chemical cross-talk between electrodes due to diffusion of electrochemically generated reagents.

Another suitable method of generating the biochip of the present invention is disclosed in Microarray Biochip Technology, ed. Mark Schena (Natick, Mass.: Eaton Publishing 2000); and Duggan, D. J., Bittner, M., Chen, Y., Meltzer, P. and Trent, J. M. (1999). Expression Profiling Using cDNA Microarrays, *Nature Genetics* Vol. 21S, p. 10-14.

Other methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 which disclose methods of forming vast arrays of peptides, oligonucleotides and other molecules using for example, light-directed synthesis techniques. See also, Fodor et al., *Science*, 251:767-777 (1991). These procedures for synthesis of polymer arrays are now referred to as VLSIPS™ procedures. Using the VLSIPS™ approach, one heterogeneous array of polymers is converted through simultaneous coupling at a number of reaction sites, into a different heterogeneous array.

The development of VLSIPS™ technology is considered pioneering technology in the fields of combinatorial synthesis and screening of combinatorial libraries. In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidite. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform synthetic steps, since the monomers do not attach to one another via a phosphate linkage. Instead, peptide synthetic methods are substituted. See, e.g. Pirrung et al., U.S. Pat. No. 5,143,854.

Peptide substituted nucleic acids are commercially available from e.g. Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In accord with the present invention, large arrays can be generated using presynthesized oligonucleotides laid down in linear rows to form an array, which then can be divided or cut into strips, to form a number of smaller, uniform arrays. Strips from different arrays can be combined to form more complex composite arrays. In this way, both the efficiency of oligonucleotide attachment (or synthesis) is improved, and there is a significant increase in reproducibility of the arrays.

It is also a desired embodiment of the present invention to provide regions having varying widths and lengths of attached oligonucleotides. Each oligonucleotide can form an oligonucleotide strip that is longer than it is wide; that is, when hybridization to a target sequence occurs, a strip of hybridization occurs. This significantly increases the ability to distinguishing over non-specific hybridization and background effects when detection is via visualization, such as through the use of radioisotope detection. When other types of detection such as fluorescence is used, the length of the strip allows repeated detection reactions to be made, with or without slight variations in the position along the length of the strip. Averaging of the data points allows the minimization of false positives or position dependent noise such as dust, microdebris, etc.

Thus, the present invention also provides for oligonucleotide arrays comprising a solid support with a plurality of different oligonucleotide pools. By "plurality" herein is meant at least two different oligonucleotide species, with from about 10 to 1000 being preferred, and from about 50 to 500 being particularly preferred and from about 100-200 being especially preferred, although smaller or larger number of different oligonucleotide species may be used as well. As will be appreciated by those in the art, the number of oligonucleotides per array will depend in part on the size and composition of the array, as well as the end use of the array. Thus, for certain diagnostic arrays, only a few different oligonucleotide probes may be required; other uses such as cDNA analysis may require more oligonucleotide probes to collect the desired information.

The composition of the solid support may be anything to which oligonucleotides may be attached, preferably covalently, and will also depend on the method of attachment. Preferably, the solid support is substantially nonporous; that is, the oligonucleotides are attached predominantly at the surface of the solid support.

Accordingly, suitable solid supports include, but are not limited to, those made of plastics, resins, polysaccharides, silica or silica-based materials, functionalized glass, modified silicon, carbon, metals, inorganic glasses, membranes, nylon, natural fibers such as silk, wool and cotton, and polymers. In some embodiments, the material comprising the solid support has reactive groups such as carboxy, amino, hydroxy, etc., which are used for attachment of the oligonucleotides. Alternatively, the oligonucleotides are attached without the use of such functional groups, as is more fully described below. Polymers are preferred, and suitable polymers include, but are not limited to, polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate and polymethylpentene. Other preferred polymers include those well known in the art, see for example, U.S. Pat. No. 5,427,779.

The solid support has covalently attached oligonucleotides. By "oligonucleotide" or "nucleic acid" or grammatical equivalents herein is meant at least two nucleotides covalently linked together. A nucleic acid of the present invention will generally contain phosphodiester bonds, although in some cases, a nucleic acid may have an analogous backbone, comprising, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate, phosphorodithioate, phosphoramidate, O-methylphophoroamidite linkages (see Eckstein, Oligonucleotides and Analogues: A Practical Approach, Oxford University Press), peptide nucleic acid linkages (see Egholm, *J. Am. Chem. Soc.* 114:1895 (1992); Meier et al., *Chem. Int. Ed. Engl.* 31:1008 (1992); Nielsen, *Nature,* 365:566 (1993)) or morpholino-type backbones. These modifications of the ribose-phosphate backbone may be done to increase the stability and half-life of such molecules in physiological environments, or to increase the stability of the hybridization complexes (duplexes). Generally, the attached oligonucleotides are single stranded. The oligonucleotide may be DNA, both genomic and cDNA, RNA or a hybrid, where the oligonucleotide contains any combination of deoxyribo- and ribonucleotides, and any combination of uracil, adenine, thymine, cytosine and guanine, as well as other bases such as inosine, xanthine and hypoxanthine.

The length of the oligonucleotide, i.e. the number of nucleotides, can vary widely, as will be appreciated by those in the art. Generally, oligonucleotides of at least 6 to 8 bases are preferred, with oligonucleotides ranging from about 10 to 500 being preferred, with from about 20 to 200 being particularly preferred, and 40 to 100 being especially preferred. Longer oligonucleotides are preferred, since higher stringency hybridization and wash conditions can be used, which decreases or eliminates non-specific hybridization. However, shorter oligonucleotides can be used if the array uses levels of redundancy to control the background, or utilizes more stable duplexes.

The arrays of the invention comprise at least two different covalently attached oligonucleotide species, with more than two being preferred. By "different" oligonucleotide herein is meant an oligonucleotide that has a nucleotide sequence that differs in at least one position from the sequence of a second oligonucleotide; that is, at least a single base is different. If the desired pattern is comprised of parallel lines, arrays can be made wherein not every strip contains an oligonucleotide. That is, when the solid support comprises a number of different support surfaces, such as fibers, for example, not every fiber must contain an oligonucleotide. For example, "spacer" fibers (or rows, when a single support surface is used) may be used to help alignment or detection. In a preferred embodiment, every row or fiber has a covalently attached oligonucleotide. In this embodiment, some rows or fibers may contain the same oligonucleotide, or all the oligonucleotides may be different. Thus, for example, it may be desirable in some applications to have rows or fibers containing either positive or negative controls, evenly spaced throughout the array, i.e., every nth fiber or row is a control. Similarly, any level of redundancy can be built into the array; that is, different fibers or rows containing identical oligonucleotides can be used.

The space between the oligonucleotide strips, or spots, etc, can vary widely, although generally is kept to a minimum in the interests of miniaturization. The space will depend on the methods used to generate the array; for example, for woven arrays utilizing fibers, the methodology utilized for weaving can determine the space between the fibers.

Each oligonucleotide pool or species is arranged in a desired pattern design, such as for example, a linear row to form an immobilized, distinct, oligonucleotide strip. By "distinct" herein is meant that each row is separated by some physical distance. By "immobilized" herein is meant that the oligonucleotide is attached to the support surface, preferably covalently. By "strip" herein is meant a conformation of the oligonucleotide species that is longer than it is wide. When the array comprises a number of different support surfaces, such as outlined above for fibers, each strip is a different fiber. However, the arrays can be arranged in any desired pattern.

In one embodiment, the solid support comprises a single support surface. That is, a plurality of different oligonucleotide pools are attached to a single support surface, in distinct linear rows, forming oligonucleotide strips. In a preferred embodiment, the linear rows or stripes are parallel to each other. However, any conformation of strips or desired patterns can be used as well. In one embodiment, there are preferably at least about 1 strip per millimeter, with at least about 2 strips per millimeter being preferred, and at least about 3 strips per millimeter being particularly preferred, although arrays utilizing from 3 to 10 strips, or higher, per millimeter also can be generated, depending on the methods used to lay down the oligonucleotides.

In an alternative embodiment, the solid support comprises a plurality of separate support surfaces that are combined to form a single array. In this embodiment, each support surface can be considered a fiber. Thus, the array comprises a number of fibers, each of which can contain a different oligonucleotide. That is, only one oligonucleotide species is attached to each fiber, and the fibers are then combined to form the array.

By "fiber" herein is meant an elongate strand. Preferably the fiber is flexible; that is, it can be manipulated without breaking. The fiber can have any shape or cross-section. The fibers can comprise, for example, long slender strips of a solid support that have been cut off from a sheet of solid support. Alternatively, and preferably, the fibers have a substantially circular cross section, and are typically thread-like. Fibers are generally made of the same materials outlined above for solid supports, and each solid support can comprise fibers with the same or different compositions.

The fibers of the arrays can be held together in a number of ways. For example, the fibers can be held together via attachment to a backing or support. This is particularly preferred when the fibers are not physically interconnected. For example, adhesives can be used to hold the fibers to a backing or support, such as a thin sheet of plastic or polymeric material. In a preferred embodiment, the adhesive and backing are optically transparent, such that hybridization detection can be done through the backing. In a preferred embodiment, the backing comprises the same material as the fiber; alternatively, any thin films or sheets can be used. Suitable adhesives are known in the art, and will resist high temperatures and aqueous conditions. Alternatively, the fibers can be attached to a backing or support using clips or holders. In an additional embodiment, for example when the fibers and backing comprise plastics or polymers that melt, the fibers are attached to the backing via heat treatment at the ends. The fibers, i.e., the separate support surfaces, plus the means to hold them together, together form the solid support.

In a preferred embodiment, the fibers are woven together to form woven fiber arrays. Thus, the array further comprises at least a third and a fourth fiber which are interwoven with the first and second fibers. In this embodiment, either or both of the weft (also sometimes referred to as the woof) and warp fibers contains covalently attached oligonucleotides.

If desired, the strips of different arrays can be placed adjacently together to form composite or combination arrays. A "composite" or "combination array" or grammatical equivalents is an array containing at least two strips from different arrays for a fiber array; the same types of composite arrays can be made from single support surface arrays. That is, one strip is from a first fiber array, and another is from a second fiber array. The second fiber array has at least one covalently attached oligonucleotide that is not present in said first array, i.e. the arrays are different.

The composite arrays can be made solely of alignment arrays, solely of woven arrays, or a combination of different types. The width and number of strips in a composite array can vary, depending on the size of the fibers, the number of fibers, the number of target sequences for which testing is occurring, etc. Generally, composite arrays comprise at least two strips. As will be appreciated by those in the art, the composite arrays can comprise any number of strips, and can range from 2 to 1000, with from 5-100 being particularly preferred.

The strips of arrays in a composite array are generally adjacent to one another, such that the composite array is of a minimal size. However, there can be small spaces between the strips for facilitating or optimizing detection. Additionally, as for the fibers within an array, the strips of a composite array may be attached or stuck to a backing or support to facilitate handling.

As will be appreciated by those in the art, the method of making the oligonucleotide arrays of the present invention may vary. In a preferred embodiment, oligonucleotides are synthesized using traditional and well-known methods and then attached to the support surface. Alternatively, the oligonucleotides may be synthesized on the surface, as is known in the art.

The oligonucleotides are synthesized as is known in the art, and then attached to the surface, see for example, U.S. Pat. Nos. 5,427,779; 4,973,493; 4,979,959; 5,002,582; 5,217,492; 5,258,041 and 5,263,992. Briefly, coupling can proceed in one of two ways: a) the oligonucleotide is derivatized with a photoreactive group, followed by attachment to the surface; or b) the surface is first treated with a photoreactive group, followed by application of the oligonucleotide. The activating agent can be N-oxy-succinimide, which is put on the surface first, followed by attachment of a N-terminal amino-modified oligonucleotide, as is generally described in Amos et al., Surface Modification of Polymers by Photochemical Immobilization, The 17th Annual Meeting of the Society of Biomaterials, May 1991, Scottsdale Ariz. Thus, for example, a suitable protocol involves the use of binding buffer containing 50 mM sodium phosphate pH 8.3, 15% $Na_2SO_4$ and 1 mm EDTA, with the addition of 0.1-10 pM/µl of amino-terminally modified oligonucleotide. The sample is incubated for some time, from 1 second to about 45 minutes at 37° C., followed by washing (generally using 0.4 N NaOH/0.25% Tween-20), followed by blocking of remaining active sites with 1 mg/ml of BSA in PBS, followed by washing in PBS. The methods allow the use of a large excess of an oligonucleotide, preferably under saturating conditions; thus, the uniformity along the strip is very high.

The oligonucleotides can also be covalently attached to the support surface. In an additional embodiment, the attachment may be very strong, yet non-covalent. For example, biotinylated oligonucleotides can be made, which bind to surfaces covalently coated with streptavidin, resulting in attachment.

Oligonucleotides can be added to the surface in a variety of ways. In one method, the entire surface is activated, followed by application of the oligonucleotide pools in linear rows or any other desired pattern, with the appropriate blocking of the excess sites on the surface using known blocking agents such as bovine serum albumin. Alternatively, the activation agent can be applied in linear rows, followed by oligonucleotide attachment.

Application of the oligonucleotides can be done in several ways. In a preferred embodiment, the oligonucleotides are applied using ink jet technology, for example using a piezoelectric pump. In another method, the oligonucleotides are drawn, using for example a pen with a fine tip filled with the oligonucleotide solution. If a series or pattern of dots is desired, for example, a plotter pen may be used. In addition, patterns can be etched or scored into the surface to form uniform microtroughs, followed by filling of the microtrough with solution, for example using known microfluidic technologies.

Oligonucleotide arrays have a variety of uses, including the detection of target sequences, sequencing by hybridization, and other known applications (see for example Chetverin et al., *Biotechnology*, Vol. 12, November 1994, pp 1034-1099, (1994)).

In a preferred embodiment, the arrays are used to detect target sequences in biological markers derived from animal models. The term "target sequence" or grammatical equivalents herein means a nucleic acid sequence on a single strand of nucleic acid. In some embodiments, a double stranded sequence can be a target sequence, when triplex formation with the probe sequence is done. The target sequence may be a portion of a gene, a regulatory sequence, genomic DNA, cDNA, mRNA, or others. It may be any length, with the understanding that longer sequences are more specific. As is outlined herein, oligonucleotides are made to hybridize to target sequences to determine the presence, absence, or relative amounts of the target sequence in a sample.

In a preferred embodiment, the arrays are used to detect changes in gene expression when an animal model is subjected to a drug treatment, drug discovery, evaluation of drug toxicity, drug efficacy, cell metabolism and the like. The arrays can also be designed to detect the expression or repression of genes encoding signaling proteins in metabolic pathways due to the administered drug, detect whether a certain drug results in the expression or repression of genes involved in inflammatory responses, etc.

Similarly, arrays can be generated containing oligonucleotides designed to hybridize to mRNA sequences and used in differential display screening of different tissues, or for DNA indexing. In addition, the arrays of the invention can be formulated into kits containing the arrays and any number of reagents, such as PCR amplification reagents, labeling reagents, etc.

Hybridizing Nucleic Acids to High Density Arrays

1. Probe Design

As is outlined herein, the arrays of the invention containing the oligonucleotides are contacted with a sample containing the target sequences under conditions which allow hybridization to occur. Generally, the samples are treated as is known in the art, including any sample preparation such as purification or amplification, followed by labeling of the target sequences, as is known in the art, using radioisotopes, or fluorescent or electrochemiluminescent compounds. In addition, in some embodiments, it may be desirable to chemically cross-link the two strands of the hybridization complex. The arrays containing the resulting hybridization complexes are then washed under a variety of stringency conditions ranging from low to high stringency, depending on the length and composition of the oligonucleotides. Detection of the hybridization complex proceeds as is known in the art.

The high density array will typically include a number of probes that specifically hybridize to the sequences of interest. In addition, in a preferred embodiment, the array will include one or more control probes.

The high density array chips includes "test probes." Test probes, for example, are oligonucleotides that range from about 5 to 45 or 5 to about 500 nucleotides, more preferably from about 10 to 40 nucleotides and most preferably from about 15 to about 40 nucleotides in length. In other particularly preferred embodiments the probes are 20 or 25 nucleotides in length. In another preferred embodiments, test probes are single or double stranded DNA sequences. DNA sequences are isolated or cloned from natural sources or amplified from natural sources using nature nucleic acid as templates. These probes have sequences complementary to particular subsequences of the genes whose expression they are designed to detect. Thus, the test probes are capable of specifically hybridizing to the target nucleic acid they are to detect.

In addition test probes that bind the target nucleic acid(s) of interest, the high density array can contain a number of control probes. The control probes fall into three categories referred to herein as 1) normalization controls; 2) expression level controls; and 3) mismatch controls.

Normalization controls are oligonucleotides or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe can serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however, in a preferred embodiment, only one or a few normalization probes are used and they are selected such that they hybridize well (i.e. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including but not limited to the β-actin gene, the transferrin receptor gene, the GAPDH gene and the like.

Mismatch controls can also be provided for the probes to the target genes, for expression level controls or for normalization controls. Mismatch controls are oligonucleotides probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe provides a good measure of the concentration of the hybridized material.

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence.

In addition, in a preferred embodiment, expression monitoring arrays are used to identify the presence and expression (transcription) level of genes which are several hundred base pairs long. For most applications it is useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

In a preferred embodiment, it is desirable to choose a preferred or optimum subset of probes for each gene before synthesizing the high density array.

Hybridization

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37° C. (0.005% Triton X-100) to ensure hybridization and then subsequent washes are performed at higher stringency (e.g., 1×SSPE-T) at 37° C. to eliminate mismatched hybrid duplexes. Successive washes may be performed at increasingly higher stringency (e.g., down to as low as 0.25×SSPE-T at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch control, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g. Chapter 8 in P. Tijssen).

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allow for optimization of duplex stability and mismatch discrimination. One useful aspect of altering the $T_m$ arises from the fact that adenine-thymidine (A-T) duplexes have a lower $T_m$ than guanine-cytosine (G-C) duplexes due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6-diaminopurine or by using the salt tetramethyl ammonium chloride (TMACl) in place of NaCl.

Altered duplex stability conferred by using oligonucleotide analogue probes can be ascertained by following, for example, fluorescence signal intensity of oligonucleotides analogue arrays hybridized with a target oligonucleotide over time. The data allow optimization of specific hybridization conditions at for example, room temperature.

Another way of verifying altered duplex stability is by following the signal intensity generated upon hybridization with time. It has been reported that experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, for example, Laboratory techniques in Biochemistry and molecular Biology, Vol. 24: Hybridization With Nucleic Acid Probes, P. Tijssen, ed. Elsevier, N.Y., (1993)).

Labeling of Probes

In a preferred embodiment, the hybridized nucleic acids are detected by detecting one or more labels attached to the sample nucleic acids. The labels can be incorporated by any number of means well known to those of skill in the art. For example, the label can be incorporated using polymerase chain reaction (PCR). In a preferred embodiment, transcription amplification, as described above, using a labeled nucleotide (e.g., fluorescein-labeled UTP and/or CTP) incorporates a label into the transcribed nucleic acids.

Alternatively, a label can be added directly to the original nucleic acid sample (e.g., mRNA, polyA mRNA, cDNA, genomic DNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

Means of detecting such labels are well known to those of skill in the art. Thus for example, radiolabels can be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. One particular preferred method uses colloidal gold label that can be detected by measuring scattered light.

The label can be added to the target (sample) nucleic acid(s) prior to, or after hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids (see, Laboratory techniques in Biochemistry and molecular Biology, Vol. 24: Hybridization With Nucleic Acid Probes, P. Tijssen, ed. Elsevier, N.Y., (1993)).

Similarly, where the expression levels of genes have been altered in the animal model by administration of a test drug, comparison of the expression levels of the genes in the treated animal model to one which has not been treated, will reveal any deviations in the expression levels of the genes in the test animal group as compared to the untreated animal group.

Means of detecting labeled target (sample) nucleic acids hybridized to the probes of high density arrays are known to those of skill in the art. Thus, for example, where a calorimetric label is used, simple visualization of the label is sufficient. Where a radioactive labeled probe is used, detection of the radiation (e.g. with photographic film or solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a CCD camera etc) attached to an automated data acquisition system to automatically record the fluorescence signal produced by hybridization to each oligonucleotide probe on the array. Such automated systems are described in U.S. Pat. No. 5,143,854, and PCT Publication No. WO 99/32660. Use of laser illumination in conjunction with automated confocal microscopy for signal detection permits detection at a resolution of better than about 100 µm, more preferably better than about 50 µm, most preferably better than about 25 µm.

One skilled in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of fluorescence (intensity) produced by a fixed excitation illumination at each location on the array. Comparison of the absolute intensities of an array hybridized to nucleic acids form a "test" sample with intensities produced by a "control" sample provides a measure of the relative expression of the nucleic acids that hybridize to each of the probes.

One skilled in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value may be selected below which a signal is not counted as being essentially indistinguishable from background.

In addition, the provision of appropriate controls permits a more detailed analysis that controls for variations in hybridization conditions, for example, non-specific binding and the like. Thus, for example, in a preferred embodiment, the hybridization array is provided with normalization controls. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically normalization is accomplished by dividing the measured signal from the other probes in the array by the average signal produced by the normalization controls. Normalization may also include correction for variations due to sample preparation and amplification. Such normalization can be accomplished by dividing the measured signal by the average signal from the sample preparation/amplification control probes. The resulting values can be multiplied by a constant value to scale the results.

As indicated above, the high density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can be scored by the number of positive signals (either absolute or above a threshold value), the intensity of the positive signals (either absolute or above a selected threshold value) or a combination of both metrics (e.g., a weighted average).

In some preferred embodiments, a computer system is used to compare the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridization intensities of a pair of probes are substantially the same, it may indicate the gene is not expressed. However, the determination is not based on a single pair of probes, the determination of whether a gene is expressed is based on an analysis of many pairs of probes.

After the system compares the hybridization intensity of the perfect match and mismatch probes, the system indicates expression of the gene. As an example, the system may indicate to a user that the gene is either present (expressed), marginal or absent (unexpressed). Specific procedures for data analysis are described infra.

It should be understood that the probes need not be nucleic acid probes but also can be other polymers such as peptides. Peptide probes can be used to detect the concentration of peptides, polypeptides, or polymers in a sample. The probes should be carefully selected to have bonding affinity to the compound whose concentration they are to be used to measure.

In addition to high density nucleic acid arrays, other methods are also useful for massive gene expression monitoring. Differential display, described by Liang, P. and Pardee, A. B., *Science*, 257:967-971 (1992) provides a useful means for distinguishing gene expression between two samples. Serial analysis of gene expression Velculescu et al., *Science*, 270: 484-487 (1995) provides another method for quantitative and qualitative analysis of gene expression. Optical fiber oligonucleotide sensors, described by Ferguson et al., *Nature Biotechnology*, 14:1681-1684, (1996) can also be used for gene expression monitoring.

A computer system, such as that disclosed in PCT Publication No. WO 99/05323 can be used to identify genes or expressed sequence tags whose expression correlates to particular tissue types.

Methods of Monitoring Gene Expression

Generally the methods of monitoring gene expression involve (1) providing a pool of target nucleic acids comprising RNA transcript(s) of one or more target genes, or nucleic acids derived from the RNA transcript(s); (2) hybridizing the nucleic acid sample to a high density array of probes (including control probes); and (3) detecting the hybridized nucleic acids and calculating a relative expression (transcription) level.

Providing a Nucleic Acid Sample.

One skilled in the art will appreciate that in order to measure the transcription level (and thereby the expression level) of a gene or genes, it is desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to mRNA transcripts of the gene or genes, cDNA reverse transcribed from the mRNA, cRNA transcribed from the cDNA, DNA amplified from the genes, RNA transcribed from amplified DNA, and the like.

In a particularly preferred embodiment, where it is desired to quantify the transcription level (and thereby expression) of one or more genes in a sample, the nucleic acid sample is one in which the concentration of the mRNA transcript(s) of the gene or genes, or the concentration of the nucleic acids derived from the mRNA transcript(s) is proportional to the transcription level (and therefore expression level) of that gene. Similarly, it is preferred that the hybridization signal intensity be proportional to the amount of hybridized nucleic acid. Although it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where precise quantification is required appropriate controls can be run to correct for variations introduced in sample preparation and hybridization as described herein. In addition, serial dilutions of "standard" target mRNAs can be used to prepare calibration curves according to methods well known in the art. Of course, where simple detection of the presence or absence of a transcript is desired, no elaborate control or calibration is required.

In the simplest embodiment, such a nucleic acid sample is the total DNA or RNA isolated from a biological sample. The term "biological sample", as used herein, refers to a standard human disease animal model. The biological sample can be obtained by using the whole animal, or organs from the animal such as, for example, spleen, liver, kidneys, brain, spinal cord etc. Cells from the animal may also be used. The biological sample can also be of any biological tissue or fluid. Frequently, the sample will be a "clinical sample" which is a sample derived from a patient. Such samples include, but are not limited to sputum, blood, cells of the immune system, tissue or fine needle biopsy samples, urine, peritoneal fluid, and pleural fluid, or cells therefrom. Biological samples also can include sections of tissues such as frozen sections taken for histological purposes.

The nucleic acid (either genomic DNA or mRNA) is isolated from the sample according to any of a number of methods well known to those of skill in the art. One skilled in the art will appreciate that where alterations in the copy number of a gene are to be detected, genomic DNA is preferably isolated. Conversely, where expression levels of a gene or genes are to be detected, preferably RNA (mRNA) is isolated. Methods of isolating total mRNA are well known to those skilled in the art. For example, methods of isolation and purification of nucleic acids are described in detail in Chapter 3 of *Laboratory Techniques in Biochemistry and Molecular Biology: Hybridization With Nucleic Acid Probes, Part 1. Theory and Nucleic Acid Preparation*, P. Tijssen, ed. Elsevier, N.Y. (1993).

In a preferred embodiment, the total nucleic acid is isolated from a given sample using, for example, an acid guanidium-phenol-chloroform extraction method and poly $A^+$ mRNA is isolated by oligo dT column chromatography or by using (dT)n magnetic beads (see, e.g. Sambrook et al., *Molecular Cloning: A Laboratory Manual* ($2^{nd}$ ed.), Vols. 1-3, Cold Spring Harbor Laboratory, (1989), or *Current Protocols in Molecular Biology*, F. Ausubel et al., ed. Greene Publishing and Wiley-Interscience, New York (1987)). Other methods for extraction include for example, the Cesium Chloride cushion method, acid-phenol extraction, Tri-Sol®, column extraction methods or solid support extraction methods such as RNAeasy® from Qiagen. Other preferred methods also include automated systems such as for example the ABI 6700 Nucleic Acid Work Station, the Roche Magna Pure system, the Qiagen BioRobot 3000 system and the Gentra systems nucleic acid extractor.

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

Comparison of Gene Expression

Various techniques are well known in the art for comparing gene expression across different treatments and time points. For example, Differential Display Polymerase Chain Reaction (ddPCR), Subtractive Hybridization (SH), Suppression Subtractive Hybridization (SSH), Random Amplified Primer Display (RAPDs), Duplicate Colony Hybridization (DCH), Amplified Fragment Length Polymorphism (ALFP), Serial Amplification of Gene Expression (SAGE), MSSP (Lynx Therapeutics), Representation Difference Analysis of cDNA (RDA-cDNA). All of these techniques can be used in the present invention for comparison of gene expression and identification of genes.

For example, a variation on polymerase chain reaction (PCR) analysis, known as RNA fingerprinting or differential display PCR, has been used to identify messages differentially expressed in ovarian or breast carcinomas (Liang et al., 1992; Sager et al., 1993; Mok et al., 1994; Watson et al., 1994). By using arbitrary primers to generate "fingerprints" from total cell RNA, followed by separation of the amplified fragments by high resolution gel electrophoresis, it is possible to identify RNA species that are either up-regulated or down-regulated in cancer cells. Results of these studies indicate the presence of several markers of potential utility for diagnosis of breast or ovarian cancer, $\alpha_6$-integrin (Sager et al., 1993), DESTOO1 and DEST002 (Watson et al., 1994), and LF4.0 (Mok et al., 1994).

Suppression Subtractive Hybridization technology has been described by Chenchik et al. (U.S. Pat. No. 5,565,340). Other methods of subtractive hybridization, described for example, by Wigler et al. (U.S. Pat. No. 5,436,142); Hampson et al. (*Nucl. Acids Res.* 20:2899 (1992)); Yang et al. (*Anal. Biochem.* 237:109-114(1996)); Balzer et al. (*Nucl. Acids Res.* 22:2853-2854(1994)), and others, can also be employed.

Many genetic-marker technologies are also adaptable to fingerprinting, including restriction-fragment-length polymorphism (RFLP) Bostein et al (1980) *Am. J. Hum. Genet.* 32:314-331; single strand conformation polymorphism (SSCP) Fischer et al. (1983) *Proc. Natl. Acad. Sci.* USA 80:1579-1583, Orita et al. (1989) *Genomics* 5:874-879; amplified fragment-length polymorphism (AFLP) Vos et al. (1995) *Nucleic Acids Res.* 23:4407-4414; microsatellite or single-sequence repeat (SSR) Weber J L and May P E (1989) *Am. J. Hum. Genet.* 44:388-396; rapid-amplified polymorphic DNA (RAPD) Williams et al (1990) *Nucleic Acids Res.* 18:6531-6535; sequence tagged site (STS) Olson et al. (1989) *Science* 245:1434-1435; genetic-bit analysis (GBA) Nikiforov et al (1994) *Nucleic Acids Res.* 22:4167-4175; allele-specific polymerase chain reaction (ASPCR) Gibbs et al. (1989) *Nucleic Acids Res.* 17:2437-2448, Newton et al. (1989) *Nucleic Acids Res.* 17:2503-2516; nick-translation PCR (e.g., TaqMan™) Lee et al. (1993) *Nucleic Acids Res.* 21:3761-3766; and allele-specific hybridization (ASH) Wallace et al. (1979) *Nucleic Acids Res.* 6:3543-3557, (Sheldon et al. (1993) *Clinical Chemistry* 39(4):718-719) among others. Kits for RAPD and AFLP analyses are commercially available, e.g., from Perkin Elmer Applied Biosystems (Foster City, Calif.). For example, the restriction fragment length polymorphism (RFLP) technique employs restriction enzyme digestion of DNA, followed by size separation of the digested DNA by gel electrophoresis, and hybridization of the size-separated DNA with a specific polynucleotide fragment. Differences in the size of the restriction fragments to which the polynucleotide probe binds reflect sequence differences in DNA samples, or DNA polymorphisms. See Tanksley, *Biotechnology* 7:257-264 (1988).

PCR-based fingerprinting methods result in the generation of a large number of reproducible DNA fragments of specific size that can be separated, typically by gel electrophoresis. These fragments are visualized to produce a "fingerprint" of the amplified DNA. Visualization of the size-separated fragments is effected either by direct visualization, e.g., with a fluorescent dye, by hybridization with a polynucleotide probe, or by labeling the amplification products during PCR (radioactively or fluorescently) followed by detection of the labeled products in the gel.

Protein Biochips

Information on protein expression profile is very useful in identifying diagnostic and therapeutic targets. Protein arrays makes it possible to detect post-translational modifications of numerous proteins and provide a valuable tool to investigate protein and cellular regulations. Protein arrays can also be used to screen a large number of potential interactions directly and can detect interactions that take place only under certain conditions, e.g. phosphorylation. Protein arrays are, therefore, useful for a variety of applications, particularly for revealing disease mechanisms, searching for diagnostic indicators and for identifying therapeutic targets.

An example of an anti-inflammatory drug is the HK-X molecule, f-Met-Leu-Phe-Phe (SEQ ID No. 1), discussed in U.S. Pat. Nos. 6,462,020 and 6,391,856 and U.S. application Ser. No. 09/960,720, the references being incorporated herewith in their entirety. The mechanism of action of HK-X (f-Met-Leu-Phe-Phe) is by inhibition of G protein γ kinase and has been found to inactivate certain pro-inflammatory responses of human peripheral blood cells that have been stimulated by pro-inflammatory agents or molecules by binding to receptors found on pro-inflammatory mediating cells such as lymphocytes, particularly activated T-cells, and granulocytes such as mast cells, eosinophils, and basophils.

Upon binding of the G protein γ kinase inhibitory agent to its receptor, pro-inflammatory responses are inhibited. The G-protein subunits α, β, and γ are downregulated and also phosphorylation of these subunits is inhibited. Pro-inflammatory responses that can be inhibited by the agent-receptor complex are degranulation and migration of the receptor-bearing cell.

Therefore, to identify inflammatory pathways and molecules which can be repressed by certain drugs, a whole animal can be treated with mock (control), HK-X or any other drug of choice plus pro-inflammatory agents, and pro-inflammatory agents. Examples of pro-inflammatory agents useful for stimulating the cells are IL-8, N-formyl peptides, activated complement fragment (C5a), leukotriene B4 (LTB4) and platelet activating factor (PAF).

In accord with one embodiment of the present invention, a protein chip is comprised of antibodies or recombinant proteins for different peptides in the inflammatory pathway. Detection by fluorescent labeling or other means will identify the over-expression, repression or no change in level of each molecule involved in the pathway. The protein content of the PMEET-ADME protein chip also includes antibodies for proteins that are involved in ADME, toxicity and drug efficacy.

Protein arrays are based on several principles. First, a protein can be recognized and identified unambiguously by specific molecules such as antibodies, recombinant proteins and small chemicals that can specifically interact with it. Second, a protein or a small chemical can be immobilized on a solid support and the immobilized molecule still retains its ability in protein-protein interactions. Agents (antibodies, recombinant proteins, and small chemicals) can be immobilized on solid supports such as glass plates, agarose beads, or polyvinylidene difluoride (PVDF) membranes (LeGendre, 1990, *Biotechniques*, Vol. 9, No. 6, p. 788-805). Third, many different agents can be immobilized at different positions on a solid support without cross interactions among them. This insures that each agent independently interacts with its respective target protein.

The term "agents" as used herein refers to antibodies, recombinant proteins, synthesized peptides, and other chemicals immobilized on the solid support of a protein array.

In the preferred embodiments, the agents immobilized on a solid support can be antibodies, recombinant proteins, or small chemicals. Antibodies are raised by immunizing animals (e.g., rabbit, mouse, rat, goat or chicken) with antigens (proteins or peptides). A large number of antibodies (monoclonal and polyclonal) are commercially available. Recombinant proteins are constructed by using recombinant DNA techniques. Many proteins have been conveniently expressed in a recombinant form with a tag such as glutathione-S-transferase (GST) and polyhistidine (6×His), to facilitate purification and identification. Small chemicals (including but not limited to synthesized peptides) can be immobilized on a support to capture and identify specific proteins.

The term "supports" as used herein refers to the materials on which agents are deposited and immobilized.

In the preferred embodiments, the supports are as described above but can also include either plates (glass or plastics) or membranes made of nitrocellulose, nylon, or polyvinylidene difluoride (PVDF). Membranes are easier to handle and agents can be readily immobilized on them. Glass or plastic plates provide rigid support and are therefore necessary in some special applications. Essentially, any conceivable substrate may be employed in accordance with the present invention. The substrate can be biological, nonbiological, organic, inorganic, or a combination of any of these, existing as particles, strands, precipitates, gels, sheets, tubing, spheres, containers, capillaries, pads, slices, films, plates, slides, etc. The substrate can have any convenient shape, such as a disc, square, sphere, circle, etc. The substrate is preferably flat, but can take on a variety of alternative structure configurations. For example, the substrate can contain raised or depressed regions on which synthesis can take place. The substrate and its surface preferably form a rigid support on which to carry out the reactions described herein. The substrate and the area for synthesis of each individual polymer or small molecule can be of any size and shape. Moreover, a substrate can comprise different materials at different regions.

Other materials, which are preferably used as substrates include silicon nitride, silicon oxide, silicon, diamond, chalcopyrites, wurtzites, sphalerites, halites; glass, such as, cobalt glass, Pyrex glass, vycor glass, borosilicate glass and quartz; ceramics, such as, alumina, porcelain, zircon, corderite, titanates, metal oxides, clays, and zeolites; polymers, such as, paralyene, high density polyethylene, teflons, nylons, polycarbonates, polystyrenes, polyacrylates, polycyanoacrylates, polyvinyl alcohols, polyimides, polyamides, polysiloxanes, polysilicones, polynitriles, polyvinyl chlorides, alkyd polymers, celluloses, epoxy polymers, melamines, urethanes, copolymers and mixtures of any of the above with other polymers, and mixtures of any of the above with glass or ceramics; and waxes, such as, apeizon. Other substrate materials can also be used.

Agents are immobilized on a solid support directly or indirectly. Agents can be directly deposited at high density on a support, which can be as small as a microscopic slide. Agents can also be immobilized indirectly on the support. For instance, protein A or G can be printed on a support. Agents (antibodies) are then immobilized on the support through their interactions with protein A or G. The advantage of this method is that by engaging the constant regions of antibodies with protein A or G, the variable regions of the antibodies (antigen-binding domains) will be fully exposed to interact with antigens. Recombinant fusion proteins can be immobilized through the interaction between their tags and the ligands printed on the support. One most important characteristic of protein arrays is that all agents are immobilized at predetermined positions, so that each agent can be identified by its position. After agents are immobilized, the support can be treated with 5% non-fat milk or 5% bovine serum albumin for several hours in order to block non-specific protein binding.

Preferably, the molecules attached to the surface of the substrate include monomers, nucleotides, and linker molecules. All of these molecules generally bond to the substrate by covalent bonds or ionic interactions. Alternatively, all of these molecules can be bonded, also by covalent bonds or ionic interactions, to a layer overlaying the substrate, for example, a permeable membrane layer, which layer can be adhered to the substrate surface in several different ways, including covalent bonding, ionic interactions, dispersive interactions and hydrophilic or hydrophobic interactions. In still another manner of attachment, a monomer or preformed molecule may be bonded to a linker molecule that is bonded to either the substrate or a layer overlaying the substrate.

The monomers, linker molecules and pre-formed molecules used herein, are preferably provided with a chemical functional group that is protected by a protecting group removable by electrochemically generated reagents. Preferably, the protecting group is on the distal or terminal end of the linker molecule, monomer, or pre-formed molecule, opposite the substrate. That is, the linker molecule preferably terminates in a chemical functional group, such as an amino or carboxy acid group, bearing an electrochemically removable protective group. Chemical functional groups that are found on the monomers, linker molecules and pre-formed molecules include any chemically reactive functionality. Usually, chemical functional groups are associated with corresponding protective groups and will be chosen or utilized based on the product being synthesized. The molecules of the invention bond to deprotected chemical functional groups by covalent bonds or ionic interactions.

Monomers used in accordance with the present invention to synthesize the various polymers contemplated include all members of the set of small molecules that can be joined together to form a polymer. This set includes, but is not limited to, the set of common L-amino acids, the set of D-amino acids, the set of synthetic amino acids, the set of nucleotides and the set of pentoses and hexoses. As used herein, monomers include any member of a basis set for synthesis of a polymer. For example, trimers of L-amino acids form a basis set of approximately 8000 monomers for synthesis of polypeptides. Different basis sets of monomers may be used at successive steps in the synthesis of a polymer using the inventive method. The number of monomers that can be used in accordance with the inventive synthesis methods can vary widely, for example from 2 to several thousand monomers can be used, but in more preferred embodiments, the number of monomers will range from approximately 4 to approximately 200, and, more preferably, the number of monomers will range from 4-20.

Additional monomers that can be used in accordance with the invention also include the set of monomers that can be decorated, i.e., monomers to which chemical moieties can be added, such as prostaglandins, benzodiazapines, thromboxanes and leukotrienes. Combinations of monomers useful for polymer synthesis and monomers that can be decorated are also contemplated by the invention. The above-discussed monomers may be obtained in unprotected form from most any chemical supply company, and most, if not all, can be obtained in protected form from Bachem, Inc., Torrance, Calif. Phosphoramidite monomers for nucleic acid synthesis can be obtained from Applied Biosystems, Inc., Foster City, Calif.

Monomers are amino acids, preferably comprising a protective group at its amino or carboxy terminus that is removable by an electrochemically generated reagent. A polymer in which the monomers are alpha amino acids and are joined together through amide bonds is a peptide, also known as a polypeptide. In the context of the present invention, it should be appreciated that the amino acids may be the L-optical isomer or the D-optical isomer or a mixture of the two. Peptides are at least two amino acid monomers long, and often are more than 20 amino acid monomers long.

Furthermore, essentially any pre-formed molecule can be bonded to the substrate, a layer overlaying the substrate, a monomer or a linker molecule. Pre-formed molecules include, for example, proteins, including in particular, receptors, enzymes, ion channels, and antibodies, nucleic acids, polysaccharides, porphyrins, and the like. Pre-formed molecules are, in general, formed at a site other than on the substrate of the invention. In a preferred embodiment, a pre-formed molecule is bonded to a deprotected functional group on a molecule, monomer, or another pre-formed molecule. In this regard, a pre-formed molecule that is already attached to the substrate may additionally bear at least one protected chemical functional group to which a monomer or other pre-formed molecule may bond, following deprotection of the chemical functional group.

"Protective groups" as used herein, are materials that bind to a monomer, a linker molecule or a pre-formed molecule to protect a reactive functionality on the monomer, linker molecule or pre-formed molecule, which may be removed upon selective exposure to an activator, such as an electrochemically generated reagent. Protective groups that can be used in accordance with the present invention preferably include all acid and base labile protecting groups. For example, peptide amine groups are preferably protected by t-butyloxycarbonyl (BOC) or benzyloxycarbonyl (CBZ), both of which are acid labile, or by 9-fluorenylmethoxycarbonyl (FMOC), which is base labile. Additionally, hydroxy groups on phosphoramidites can be protected by dimethoxytrityl (DMT), which is acid labile. Exocyclic amine groups on nucleosides, in particular on phosphoramidites, are preferably protected by dimethylformamidine on the adenosine and guanosine bases, and isobutyryl on the cytidine bases, both of which are base labile protecting groups. This protection strategy is known as fast oligonucleotide deprotection (FOD). Phosphoramidites protected in this manner are known as FOD phosphoramidites.

As mentioned above, any unreacted deprotected chemical functional groups can be capped at any point during a synthesis reaction to avoid or to prevent further bonding at such molecule. Capping groups "cap" deprotected functional groups by, for example, binding with the unreacted amino functions to form amides. Capping agents suitable for use in the present invention include: acetic anhydride, n-acetylimidizole, isopropenyl formate, fluorescamine, 3-nitrophthalic anhydride and 3-sulfoproponic anhydride. Of these, acetic anhydride and n-acetylimidizole are preferred.

In accordance with the invention, the surface of the substrate is preferably provided with a layer of linker molecules. Linker molecules allow for indirect attachment of monomers or pre-formed molecules to the substrate or a layer overlaying the substrate. The linker molecules are preferably attached to an overlaying layer via silicon-carbon bonds, using, for example, controlled porosity glass (CPG) as the layer material. Linker molecules also facilitate target recognition of the synthesized polymers. Furthermore, the linker molecules are preferably chosen based upon their hydrophilic/hydrophobic properties to improve presentation of synthesized polymers to certain receptors. For example, in the case of a hydrophilic receptor, hydrophilic linker molecules will be preferred so as to permit the receptor to approach more closely the synthesized polymer.

The linker molecules are preferably of sufficient length to permit polymers on a completed substrate to interact freely with binding entities exposed to the substrate. The linker molecules, when used, are preferably 650 atoms long to provide sufficient exposure of the functional groups to the binding entity. The linker molecules, which may be advantageously used in accordance with the invention include, for example, aryl acetylene, ethylene glycol oligomers containing from 2 to 20 monomer units, diamines, diacids, amino acids, and combinations thereof. Other linker molecules known by those skilled in the art, may also be used.

The molecules of the invention, i.e., the monomers, linker molecules and pre-formed molecules, can be attached directly to the substrate or can be attached to a layer or membrane of separating material that overlays the substrate. Materials can include, for example, controlled porosity glass (CPG); generic polymers, such as, teflons, nylons, polycarbonates, polystyrenes, polyacrylates, polycyanoacrylates, polyvinyl alcohols, polyamides, polyimides, polysiloxanes, polysilicones, polynitriles, polyelectrolytes, hydrogels, epoxy polymers, melamines, urethanes and copolymers and mixtures of these and other polymers; biologically derived polymers, such as, polysaccharides, polyhyaluric acids, celluloses, and chitons; ceramics, such as, alumina, metal oxides, clays, and zeolites; surfactants; thiols; self-assembled monolayers; porous carbon; and fullerene materials. The membrane can be coated onto the substrate by spin coating, dip coating or manual application, or any other art acceptable form of coating.

Different protein arrays can be made for different purposes. For instance, "PMEET-ADME Cytokine Array" can be made of agents for cytokine assay. "PMEET-ADME Cell Cycle Array" can be made of agents for detecting cell cycle related factors; "PMEET-ADME Signal Transduction Array" can be made of agents for examining signaling proteins such as G-proteins; "PMEET-ADME Inflammatory Factor Array" can be made of agents that examine the inflammatory pathway; "PMEET-ADME Transcription Factor Array" can be made of agents for analyzing activators and suppressors of transcription, and the like. In order to reveal the broad protein expression pattern in a source (e.g. a cell line, medically relevant animal models), thousands of different antibodies are immobilized in a single support. The amount of antibodies immobilized also can be different, preferably in the range of nanogram to microgram. The number of different agents immobilized on one solid support varies depending on the particular applications.

Protein arrays can be applied in studying protein expression patterns. An antibody array is incubated with a protein sample prepared under the conditions that native protein-protein interactions are minimized. After incubation, unbound or non-specific binding proteins can be removed with several washes. Proteins specifically bound to their respective antibodies on the array are then detected. Because the antibodies are immobilized in a predetermined order, the identity of the protein captured at each position is therefore known. Measurement of protein amount at all positions on the array thus reflects the protein expression pattern in the sample.

The quantities of the proteins trapped on the array can be measured in several ways. First, the proteins in the samples can be metabolically labeled with radioactive isotopes ($^{35}$S for total proteins and $^{32}$P for phosphorylated proteins). The amount of labeled proteins bound to each antibody on an array can be quantitated by autoradiography and densitometry. Second, the protein sample can also be labeled by biotinylation in vitro. Biotinylated proteins trapped on the array will then be detected by avidin or streptavidin which strongly binds biotin. If avidin is conjugated with horseradish peroxidase or alkaline phosphatase, the captured protein can be visualized by enhanced chemical luminescence. The amount of proteins bound to each antibody represents the level of the specific protein in the sample. If a specific group of proteins are interested, they can be detected by agents which specifically recognize them. Other methods, like immunochemical staining, surface plasmon resonance, matrix-assisted laser desorption/ionization-time of flight, can also be used to detect the captured proteins.

Protein arrays can be applied in studying post-translational modifications such as phosphorylation, glycosylation or ubiquitination. In the preferred embodiments, arrays comprising antibodies on glass plates or membranes are used to capture cellular proteins. The phosphorylation of the proteins captured on the array can be revealed if the proteins are metabolically labeled with $^{32}$P in vivo. Alternatively, the phosphorylation can be detected by antibodies against phosphorylated amino acids. Antibodies against phosphotyrosine, phosphoserine or phosphothreonine are commercially available and used in many applications. When these antibodies are used, the phosphorylation state of a protein can be detected through a similar strategy used in immunoblotting. Similarly, the glycosylation of the many proteins captured on the array can be studied either by labeling glycoproteins with radioactive glycosylation precursors or by using molecules that specifically recognize carbohydrate moieties of glycoproteins. A family of such molecules are lectins including Concanavalin A and Wheat Germ agglutinin. To detect protein ubiquitination, antibodies specific for ubiquitin can be used.

In a preferred embodiment, the antibodies are chicken monoclonal antibodies that are tethered to a support or suspended in a gelatinous material. The use of chicken monoclonal antibodies provides an increased ability to make antibodies to mammalian proteins due to the evolutionary distance between chickens and mammals as well as a rapid method for the development of monoclonal antibodies.

Protein arrays can be applied in studying protein-protein interactions. When a protein is captured by its antibody immobilized on an array, other proteins may also be tethered to the same position due to protein-protein interaction. A protein mixture (e.g., cell lysate, proteins from medically relevant animal models) is made under such conditions that protein-protein interactions are preserved. After incubation of the protein mixture with the array, the protein of interest will be captured in the position where its interacting protein (s) is captured. By localizing the position of the interested protein, the identity of its interacting protein is known (because the identity of each agent is predetermined). The protein of interest can be localized by either its specific antibodies or other methods. The protein of interest can be expressed as a fusion protein with a tag and can then be detected by the tag's specific property. For example, a GFP fusion protein can be readily detected under UV light. Besides, using an array with a larger pool of different agents will increase the chance of detecting the interacting proteins.

In another preferred embodiment, protein arrays made of multiple recombinant proteins are used to identify protein-protein interactions. Many recombinant fusion proteins containing a tag (e.g., GST or 6xHis) at their N- or C-termini are constructed, expressed, and purified. These recombinant proteins are immobilized as agents onto the support printed with their ligands (e.g., glutathione or nickel). After incubation, the protein of interest is captured by the agents (recombinant proteins) immobilized on the array. By detecting the position where the protein of interest is captured, the identity of its interacting protein is obtained. The recombinant protein array provides a very convenient tool for detecting protein-protein interaction.

Databases and Software

Devices and computer systems have been developed for collecting information about gene expression or expressed sequence tags (EST) in large numbers of samples. The PMEET-ADME process will produce copious amounts of data (gene and protein expression profiles in response to treatments in numerous animal models) that will be stored in databases. These databases can be mined (using commercially available software programs or as described below) for genes and proteins that correlate with numerous responses and projections as to involvement in pathways can be made. From this information the RNA expression shift that occurs in diseases can be studied and evaluated for markers that could be used as diagnostics to indicate the coming disease or condition. In the same manner, the databases are used to identify genes and proteins that would be good candidates for therapeutic intervention during a disease state or condition.

In order to derive full benefit from the investment made in collecting and storing expression data, techniques enabling one to efficiently mine the data to find items of particular relevance are highly desirable.

A preferred embodiment of the database, referred to as Drug-Gene-Protein-Biology Database (DGPB) links drug action, genetic response, protein response and biological response together providing information storage and software tools to compare and analyze data. As the information in the database expands, the information in the database is mined allowing for the ability to predict the biological response of a new drug based on the genes and proteins that demonstrate induction or repression. In another preferred embodiment the database is mined for the identification of new drug targets, new biological switches, new biological pathways, and the actions of drugs and drug treatments across a wide gene and protein profile.

Another preferred embodiment of the ability of the database is to categorize the information such as gene expression, protein profiling, and the like, by animal models. In another preferred embodiment the information is sub-categorized based on diseases and similarity of gene expression, protein profiling and the like. Any information can be mined by searching for example, disease categories and which genes and proteins are expressed or repressed depending on the drug used; comparison of the different gene and protein profiles between the different animal models subjected to the same or different drug; biochemical pathways can be compared; inflammatory pathways, etc. The DGPB database is preferably able to categorize and link data obtained using the biochips from medically relevant models of human diseases to gene, protein, and metabolic profiling.

Any commercial software programs may be used for database mining. However, the preferred model is a database that has the ability to organize expression or concentration information in a way that facilitates mining. A preferred database model organizes information relating to, e.g., sample preparation, expression analysis of experiment results, and intermediate and final results of mining gene expression measurements, gene sets and the like. The model is readily translatable into database languages such as SQL and the like. The database model can scale to permit mining of gene expression measurements collected from large numbers of samples.

According to an embodiment of the present invention, a computer based method for mining a plurality of experiment information is provided. The method includes a variety of steps such as collecting information from experiments and chip designs. The method can include steps of selecting experiments to be mined. Experiment results and other information can be organized by experimental analysis, and the like. A step of defining one or more groupings for the experiments to be mined is also part of the method. The method also includes a step of selecting based upon the groupings, information about the experiments to be mined to form a plurality of resulting information. This resulting information can include one or more resulting gene sets, and the like. Finally, the method formats the resulting information for viewing by a user. The combination of these steps can provide to the user the ability to access experiment information.

Visualization techniques can be used in conjunction with the steps of the method to enable users to more easily understand the results of the data mining. In further embodiments, a step of recording conclusions about the results of the data mining can also be part of the method.

Mining the database for expression information includes a variety of steps such as collecting information about results of experiments; a step of gathering information about samples and information about the experiments, which can comprise an experimental analysis and the like, is also part of the method; the step of adding one or more attributes to the information about the experiments can also be performed. The method then transforms the plurality of results of experiments into a plurality of transformed information. Transformations can include normalizing, de-normalizing, aggregation, scaling, and the like. Steps of mining the plurality of transformed information and visualizing the plurality of transformed information can also be part of the method.

One embodiment of the present invention operates in the context of a system for analyzing biological or other materials using the above-described chips. Experimental information obtained from the biochips is inputted into the database. Optionally, information regarding a specific genetic sequence of interest may be downloaded from external databases such as GenBank.

In an experimental format, a sample to be analyzed is exposed to probes as described above. For example, on a oligonucleotide based chip, the nucleotides may or may not bind to the probes. The nucleotides are tagged with fluorescein labels to determine which probes have bonded to nucleotide sequences from the sample. The prepared samples are placed in a scanning system. The scanning system includes, for example, a detection device such as a confocal microscope or CCD (charge-coupled device) that is used to detect the location where labeled receptors have bound to the substrate. The output of scanning system is an image file(s) indicating, in the case of fluorescein labeled receptor, the fluorescence intensity (photon counts or other related measurements, such as voltage) as a function of position on the substrate. Because higher photon counts will be observed where the labeled receptor has bound more strongly to the array of polymers, and because the monomer sequence of the polymers on the substrate is known as a function of position, it becomes possible to determine the sequence(s) of polymer(s) on the substrate that are complementary to the receptor.

The image files and the design of the chips are inputted to an analysis system that, for example, calls base sequences, or determines expression levels of genes or expressed sequence tags. The expression level of a gene or EST is herein understood to be the concentration within a sample of mRNA or protein that would result from the transcription of the gene or EST. For example, such analysis techniques are disclosed in WO97/10365 and U.S. Pat. No. 5,974,164.

The DGPB database maintains information used to analyze, for example, expression and the results of expression analysis. Contents of the database can include tables listing analyses performed, analysis results, experiments performed, sample preparation protocols and parameters of these protocols, chip designs, etc.

An aspect of the database is that it contains information resulting from the PMEET-ADME biochip experimentation. For example, the database may contain information concerning the expression of many genes or ESTs, protein expression, metabolic profiling, etc. To mine the data, the database may include duplicate representations of data in expression analysis database. The database may also include various tables to facilitate mining operations conducted by a user who operates a querying and mining system. The querying and mining system includes a user interface that permits an operator to make queries to investigate expression of genes, proteins etc., that are influenced by drugs in the medically relevant animal model. One or more computers may maintain DGPB database.

The computer system maintaining the database can be a single computer or a system of computers and can be accessed through various interface systems well known in the art. A network interface may provide a direct connection to a remote server via a telephone link or to the Internet. The network interface can also connect to a local area network (LAN) or other network interconnecting many computer systems.

The database is preferably a multidimensional relational database with a complex internal structure. However, other types of databases can also be used without departing from the scope of the present invention.

It can be useful to identify genes or ESTs, proteins, etc., whose expression varies in some way depending on one or more drug attributes administered to the medically relevant animal models. Therefore, it is necessary for querying and mining system to have awareness of drug attributes associated with expression analysis results. In a presently preferable embodiment, expression analyses can be conducted on experiment data according to one or more selectable criteria to produce experimental analysis result data.

Associated with experimental samples are attributes. Some of the attributes are strings or values identifying concentrations, sample preparation dates, expiration dates, and the like. Other attributes identify characteristics that are highly useful in searching, for example, for genes of interest; diseases; disease progression in a medically relevant animal by comparing time points; the disease state of tissue, the organ, or species from which a sample is extracted. A sample can have more than one attribute, and an attribute can describe more than one sample item.

Each attribute has an associated attribute type and an associated value for the attribute. Examples of attribute types are "concentration," "preparation date," "expiration date," etc. Another example of an attribute type would be "specimen type" where possible values would correspond to "tissue," "organ culture," "purified cells," "primary cell culture," "established cell line," "drug of choice" and the like.

Certain attribute types can derive from other attribute types. For example, the attribute type "medically relevant animal model" can be derived from an attribute type "inflammation" which is in turn derived from an attribute "disease." Some attribute types have no associated attributes but rather define levels of categorization. The derivations relating a "parent" attribute type to a "child" attribute type can include one or more parents or children. One representative attribute type derivation type is category-subcategory where the parent type represents a category such as, for example, "drug" and the child type represents the subcategory, for example, "gene expression". The availability of derivation relationships among attribute types greatly facilitate the formulation of useful queries to mining the database, allowing the user to readily identify attribute types of interest.

The database can also be organized in table format relating to information about experiments. An experiment table lists experiments whereby results are available for querying. For example, a data map table lists entries corresponding to sets of genes or proteins that may be induced by a particular drug across a spectrum of animal models. Each set corresponds to a collection of experiments performed to investigate the genes, proteins, toxic side effects etc., in the set, and thus defines the collection of experiments corresponding to each gene set, or protein set, etc. An analysis set table defines sets of analyses that have been performed corresponding to each gene or protein set, for example. Each entry defines an association between an analysis, an experiment and an entry in data map table.

It is also highly desirable to have information in the DGPB database regarding housekeeping genes, that is, genes with known expression level that are used to calibrate the expression monitoring process.

Tables related to analysis information are also a preferred method of organization of data. The data may be organized according to "absolute result" or "relative result". Different absolute result types may include e.g., present, marginal, absent, and unknown, indicating an estimate of the expression level of a given gene or EST, protein expression or lack thereof, efficacy of drug, toxicity, etc. Relative analyses compare expression of a gene, protein etc, between, at least, two experiments. Different relative result types may include e.g., increased, no change, decreased, and unknown, all describing the change of expression.

Querying and mining systems also perform various expression analysis operations. Each entry in a criteria set table identifies a set of criteria used to query a group selected by sample item or by attribute. Each entry in a criteria set experiment table identifies a set of criteria applied to gene, protein, EST expression levels, toxicity etc., of a particular sample item belonging to a group identified by reference.

Various other tables can be included such as a user preferences table which stores references to user preference files that record the preferences of individual users. Users may wish to store functions used for normalization of expression data for later use.

A simple illustration of the process steps for mining a plurality of experimental information is as follows. This illustration should not limit the scope of the invention and one of ordinary skill in the art would recognize other variations, modifications, and alternatives. In a first step, information from experiments and chip designs is collected. Then, in a second step, experimental analyses to mine are selected. In a third step, one or more sample attributions are defined. In a third step, resulting information is determined from the experimental analyses by mining to form a plurality of resulting information. This resulting information can include one or more resulting gene sets or any other information required by the user. A final step formats the resulting information for viewing by a user. The combination of these steps can provide to the user the ability to access experimental information.

Determination of an Unknown Genes' Function Through the Use of Orthologous Gene Databases:

During the process of determining and identifying genes and proteins for biochip content it is possible that a number of the genes and proteins will have novel functions, novel drug response or novel expression patterns. By further studying (sequencing and database searching) these genes and proteins may be recognized as previously unidentified or the function or expression of these genes and proteins maybe identified as novel. Furthermore by searching orthologous databases a function for the novel gene or protein maybe identified. Additionally, genes and proteins of previously unknown function may have their gene or protein function assigned to them through the searching of the orthologous databases and comparison to the PMEET-ADME databases. As an example, a gene previously identified to be expressed in a limb of a lower eukaryotic organism maybe be linked to, or shown to be responsible for a negative or positive response to a drug in a target organ, for example. Thus, a gene that was previously shown only to be expressed in a limb of a distantly related species is linked to, or, shown to be responsive to a drug.

In order that the invention described herein may be more fully understood, the following examples are set forth. It should be understood that these examples are for illustrative purposes only and are not to be construed as limiting this invention in any manner.

EXAMPLES

Materials and Methods

In Situ Hybridization, Immunocytochemistry and Cytochemistry

In situ hybridization, immunocytochemistry and cytochemistry include methods well known in the art. See Mitchell et al., "In situ hybridization: a review of methodologies and applications in the biomedical sciences," Medical Laboratory Sciences, vol. 49, pp. 107-118 (1992). Martinez et al., "Non-radioactive Localization of Nucleic Acids by Direct In Situ PCR and In Situ RT-PCR in Paraffin-embedded Sections," Journal of Histochemistry and Cytochemistry, vol. 43, 1995. Oosterwijk et al., "Expression of Intermediate-sized Filaments in Developing and Adult Human Kidney and Renal Cell Carcinoma," The Journal of Histochemistry and Cytochemistry, 38(3): 385-392 (1990).

To directly visualize enzyme pathways, labeled inhibitors are used to directly visualize the cellular distribution of the target protease. The label can be fluorescent for fluorescence microscopy, radioactive for autoradiography, or electron dense for electron microscopy. The target structures can be whole cells, cells fixed onto slides or sections through solid tissue. A useful modification of these techniques is to use an indirect ("sandwich") assay employing the specific high affinity interaction between biotin and avidin (reviewed in Methods in Enzymology, vol. 184, 1990). Commercially available kits may be used e.g. to test for alkaline phosphatase activity, cells are fixed in 80% ethanol (Buehr and McLaren, Meth. Enzymol. 225: 58-77, 1993) and stained employing a protocol from an AP cytochemistry kit (Sigma Chemical Co., St. Louis, Mo.).

Immunoblots and immunohistochemistry can be performed according to the method of Bronstein, et al. (Bronstein, J. M., Wasterlain, C. G., Lasher, R., Bok D., Farber, D. B., "Localization of Retinal Calmodulin Kinase," Exp Eye Res. 47:391-402 (1988), incorporated herein by reference in its entirety)

In situ hybridization can be performed using $^{35}$S-labeled cRNA probes by the method of Angerer et al. (Angerer, L. M., Stoler, M. H., and Angerer, R. C., "In Situ Hybridization With RNA Probes: An Annotated Recipe." In K. L. Valentino, J. H. Eberwine, and J. D. Barches (Eds) "In Situ Hybridization," Oxford University Press 43-70 (1987), incorporated herein by reference in its entirety) as modified by Popper et al. (Popper, P., Ulibarri, C., and Micevych, P. E., "The Role of Target Muscles in the Expression of Calcitonin Gene-Related Peptide mRNA in the Spinal Nucleus of the Bulbocavernosus," Mol. Brain. Res. 13:43-51 (1992), incorporated herein by reference in its entirety). Oligodendrocyte cultures can be enriched according to the method of Suzumura et al. (Suzumura, A., Bhat, S., Eccleston, P. A. et al., "The Isolation and Long-Term Culture of Oligodendrocytes From Newborn Mouse Brain," Brain Res. 324:379-383 (1984), incorporated herein by reference in its entirety). These cells can be treated in a similar manner as brain slices for in situ hybridization.

Preparation of Immunized Animal Models

Immunized animal models are prepared using the currently available standard techniques. This includes but is not limited to the techniques of using an adjuvant to increase the antigenicity of an antigen. The antigen can be either injected into the animals muscle, stomach, blood, applied intra-nasally or topically, feed to the animal or through the surgical process of introduction through the spleen.

Animal models are also prepared surgically, by using the application of standard techniques and procedures. These techniques include, but are not limited to, the grafting of biological material from one animal to another, the removal of a portion of an animal, the occlusion of a vein, artery, duct, gland or opening. Additionally, the damaging of a normal tissue, gland or organ using a surgical means to reduce, limit or restrict normal function is included.

Selection of Positive Control and Negative Control Drugs

Part A: Positive Control Drug Selection

Positive control drugs are selected based on their properties of efficacy, therapeutic index, few side effects, low toxicity and desirable ADME properties (Absorption, Distribution, Metabolism, and Elimination) in the selected medically relevant disease model. Typically the positive control drugs are drugs that are the standard of care used in the medical community for treatment of the disease that the medically relevant animal model reflects. However, some drugs have a very high therapeutic response but may also have undesirable toxicity and/or side effects.

Part B: Negative Control Drug Selection

Negative control drugs are selected based on their properties of toxicity, side effects and low, or lower efficacy than the current standard of care used by the medical community for treatment of the disease that the medically relevant animal model reflects. These negative control drugs, for example, are drugs that failed to be successful in FDA phase I, II or III trails for the disease that the medically relevant animal model reflects. Additionally, these negative drugs are drugs that have never been in FDA phase I, II or III trails due to their failure in the pre-clinical trail model(s), including the medically relevant animal model that it is being used as a negative control for in the PMEET-ADME experiments. Typically, the negative control drugs will have a undesirable toxicity, or an undesirable toxicology, or an undesirable ADME (Absorption, Distribution, Metabolism and Elimination) profile, or undesirable side effects, or a low therapeutic index, or a combination of the previously listed undesirable properties. Examples of such drugs are listed in Table 6.

TABLE 6

Examples of drugs that have been discontinued or terminated in FDA trials.

| Drug | Company | Indication | Termination |
|---|---|---|---|
| Colloral | Autoimmune Technologies LLC | Rheumatoid Arthritis | Results were equal to placebo |
| DHEA | Neuricrine Biosciences | Alzheimer's Disease | Results were equal to placebo |
| ENBREL | Immunex Corporation | Congestive Heart Failure | Lack of efficacy |
| Idoxifene | Glaxo SmithKline | Osteoporosis | Lack of efficacy |
| Idoxifene | GlaxoSmithKline | Breast Cancer | Lack of efficacy |
| Lisofylline | Cell Therapeutics | Acute Respiratory Disease | Safety Board recommendation |

Part C: Determination of Chemical Hazards

The determination of a chemical's toxicology and hazardous profile is performed by replacing the positive, negative and candidate drugs with the chemicals for evaluation. In this case the positive control would be no treatment or mock treatment and the negative control would be a chemical with known toxicology and hazard profile. Examples of representative chemicals are listed in Table 7.

TABLE 7

Examples of hazardous chemicals

| Chemical | Hazard |
|---|---|
| Formaldehyde | Inhalation and contact |
| Paraformaldehyde | Inhalation and contact |
| Acrdine orange | Mutagen |
| Ethidium Bromide (EtBr) | Mutagen |
| Hydrochloric Acid (HCl) | Inhalation and Contact |
| Sodium Hydroxide | Inhalation and Contact |
| Methanol | Ingestion and Contact |
| Ethanol | Ingestion and Contact |
| Acetone | Ingestion and Contact |
| Sodium Dodecyl Sulphate (SDS) | Inhalation and Contact |

TABLE 7-continued

Examples of hazardous chemicals

| Chemical | Hazard |
| --- | --- |
| Dextran Sulphate | Inhalation |
| Saponin | Inhalation and Contact |
| Tetra Methyl Ammonium Chloride (TMAC) | Inhalation, Ingestion and Contact |
| Tetra Ethyl Ammonium Chloride (TEAC) | Inhalation, Ingestion and Contact |
| Acids (General) | Inhalation, Ingestion and Contact |
| Bases (General) | Inhalation, Ingestion and Contact |
| Detergents (General) | Inhalation, Ingestion and Contact |
| Salts (General) | Inhalation, Ingestion and Contact |
| Powders (General) | Inhalation, Ingestion and Contact |
| Organics (General) | Inhalation, Ingestion and Contact |
| Inorganics (General) | Inhalation, Ingestion and Contact |

Selection of Biochip (Gene Chip and Protein Chip) Content

The PMEET-ADME process preferably involves the application of a two-chip system to determine the efficacy, toxicity and ADME of a drug. This is desirable due to the presence of a translational control existing between the expressed RNA and the translated protein as well as the fact that modification of proteins results in an alteration of the proteins' activities. Thus an understanding of the proteins' state and the genetic state of the organism is preferred.

Determination or selection of biochip content preferably is based on the comparison of gene expression and protein expression across the development of the diseased state in the medically relevant animal model as well as the gene expression and protein expression in the diseased state as it responds to medical treatment. These medical treatments include a positive control drug, i.e., one that should ameliorate the diseased state and a negative drug, i.e., one that has undesirable properties such as toxic effects, induction of additional diseased states or an increase or exacerbation of the model diseased state. The identification of biochip content, for both the gene and protein chips, utilizes comparisons made between normal animals versus diseased animals versus treated diseased animals. Additional comparisons between time-points within a treated or untreated diseased state are performed. The rationale behind the comparison of the treatment groups within a time-point is that it allows identification of differentially expressed genes and proteins that produce or are involved in the production of the diseased state as well as in the amelioration or reduction of the diseased state. Comparison of the treatment groups across time-points, thus, allows for the identification of the genes and proteins involved in the severity of the disease or the amelioration of the disease depending on the treatment group that is being evaluated.

An illustrative gene expression experiment is set up as follows, using medically relevant disease animal models. The animals are randomly sorted out into: Control (No-disease); Diseased mock treatment control (drug vehicle only); Diseased positive treatment control (Positive drug treatment); Diseased negative treatment control (Negative drug treatment); Diseased candidate treatment(s) (Candidate drug treatment groups); wherein each group is comprised of multiple numbers of animals.

Time points to compare gene and protein expression between normal and diseased animals are selected. In general, these time-points are at the initial stage of the medically relevant disease, at the full development or complete involvement of the disease, and at several time-points intermediate of the disease induction and the fully involved disease. Thus the time points allow the study of the disease progression in a pathological fashion.

Organs involved in the disease or the organs afflicted by the disease (normal, diseased and treated organs) are harvested. As an example, in a murine asthma model, the lungs are the organs that are harvested. Harvested organs from each group are either randomly distributed to three sub-groups (gene expression, protein expression or standard practices) or each organ from each mouse is divided into thirds and each third is placed in one of three sub-groups (gene expression, protein expression and standard practices). Genes, proteins and fragments thereof are extracted and purified as described above. For example, the RNA from each of the subgroups can be extracted using one of a number of different standard methods. These methods include, but are not limited to, the Cesium Chloride cushion method, the Acid-Phenol method, the Tri-Sol® method and numerous different column extraction methods or solid support extraction methods (e.g. RNAeasy® from Qiagen). Additionally, automate systems are now available that makes the extraction of nucleic acids from biological material a high-through put process. Examples of these systems include the ABI 6700 Nucleic Acid Work Station, the Roche Magna Pure system, the Qiagen BioRobot 3000 system and the Gentra systems nucleic acid extractor. The extracted RNA is maintained in a standard method that prevents lose or degradation of the RNA. One standard method for this is as a precipitated pellet in a plastic microfuge tube that has low nucleic acid adhesion. Commonly the pellet is stored under 100% Ethanol at −80° C. and sealed shut to prevent evaporation. Once all of the gene expression subgroup samples from each control and treatment group from a single time-point has had the RNA extracted from the biological material, the individual subgroup samples are checked for degradation, or intactness, and the quantity of the RNA is determined. The standard method for quantifying a nucleic acid sample is spectrophotometrically ($A_{260}$) and the standard method for determining intactness is a denaturing gel electrophoresis followed by Northern Blot and Hybridization using a labeled (radioactive or non-radioactive label; isotopic or non-isotopic) antisense gene that is well characterized and studied such as Actin or GAPDH. Conversely, the intactness and quantity of the nucleic acid can be determined using one of the new "Lab-on-a-chip" systems that are available. An example of one of these instruments is the Agilent Bioworkstations.

From the extracted and intact RNA, a first strand cDNA synthesis is synthesized either by using one of the standard procedures of using individual purchased reagents and either the reverse AMV or MMULV transcriptases or a commercially available cDNA synthesis kit or a commercially available double stranded cDNA synthesis kit. The first strand synthesis cDNA can be generated from total RNA or from mRNA. In the second case (mRNA) the poly A+ fraction of the total RNA will need to be purified using the standard technique of Oligo dT column purification or using one of the many commercial kits that are available. After first strand cDNA synthesis is complete, the synthesis of $2^{nd}$ strand DNA can commence. Once again, this can use the standard procedure and individual purchased reagents or the $2^{nd}$ strand synthesis can be carried out using any of the commercially available kits.

The following diagram is an illustrative example of the design of an array or matrix and is not meant to be construed as a limitation, thereof, in any way. For example, for comparison of the RNA expression profiles between normal; diseased; and, diseased+treatments; at the selected time-points requires that a comparison between the different treatments and disease states at the selected time-points as well as between the different time-points be performed. The comparisons are visualized in the context of a two-dimensional array or matrix.

decrease or loss. For example, disease progression or disease development genes are selected based on the comparison of the normal animals gene expression profile to the mock treated diseased animals gene expression profile. Induction or upregulation of a gene's expression or genes' expression in a

| Disease state and treatment | | Time-points for harvesting organs | | | | | | | | | | | |
|---|---|---|---|---|---|---|---|---|---|---|---|---|---|
| Disease State | Treatment | 1 | 2 | 3 | 4 | 5 | 6 | 7 | 8 | 9 | 10 | 11 | 12 |
| Normal | None | + | + | + | + | + | + | + | + | + | + | + | + |
| Diseased | Mock | + | + | + | + | + | + | + | + | + | + | + | + |
| Diseased | Positive* | − | − | − | − | + | + | + | + | + | + | + | + |
| Diseased | Negative* | − | − | − | − | + | + | + | + | + | + | + | + |
| Diseased | Candidate 1*# | − | − | − | − | + | + | + | + | + | + | + | + |
| Diseased | Candidate 2*# | − | − | − | − | + | + | + | + | + | + | + | + |

+ Indicates that samples were harvested from the medically relevant animal model.
− Indicates that samples were not harvested from the medically relevant animal model.
*The assumption is that the first few time-points are intermediate in the expression of the disease. Therefore, the time-points are collected to study the disease and provide a baseline for the future time-point comparisons.
The number of candidate drugs in an experiment is more dependent upon the size and the ability to handle increasing numbers of samples and not the actual numbers of candidate or control drugs used in the experiment.

The RNA expression profile comparisons occur down the columns and across the rows. As RNA expression profiling occurs down the rows between normal and mock treated diseased animals, any RNA's that are differentially (induced or repressed) regulated during the development of the disease, during disease progression and in the fully developed disease are revealed. Comparison of the RNA profiling between time-points for the mock treated diseased control reveal gene expression that is involved in the development of the disease. The expansion of the comparisons down the rows to include the positive and negative treatments of the diseased animals identifies the genes that are involved in the amelioration of a disease state (positive drug control) and the genes that involved in the exacerbation (negative drug control) of a diseased state. The comparison of the gene and protein expression profiles between the control treatments to the diseased animal model and the treatments of the candidate drugs evaluates the candidate drugs' efficacy and toxicity.

The gene and protein expression comparisons are also compared in multiple organs. For example, the organs that are subjected to gene and protein expression profiling are those organs that are involved in systemic detoxification of the body, organs that are involved in the movement of the drug, organs that would be the targets of a drugs toxicity and the organ that is the target organ for the disease. As an example, in a murine asthma model the organs that are evaluated, include (but are not limited to) the lungs, stomach, intestine, heart, kidney, liver and the central nervous system. Thus the previous two dimensional table becomes a multi-layered matrix composed of a table for each organ.

The gene expression methods (and modifications of or alterations of) that are used to compare gene expression across the different treatments and time-points are as described supra. For example, Differential Display Polymerase Chain Reaction (ddPCR); Subtractive Hybridization (SH); Suppression Subtractive Hybridization (SSH); Random Amplified Primer Display (RAPDs); Duplicate Colony Hybridization (DCH); Amplified Fragment Length Polymorphism (ALFP); Serial Amplification of Gene Expression (SAGE); MSSP (Lynx Therapeutics); Representation Difference Analysis of cDNA (RDA-cDNA).

Selection of gene content for the gene expression biochip occurs by selecting the genes that fit into the categories of disease progression or development and healthy state medically relevant diseased animal model indicates that the induced gene is involved with the induction of the disease state. Especially relevant are those genes that are induced early in the development of the disease before any disease symptoms can be detected or those genes induced early in the disease process. Genes that have an induced gene expression profile or an upregulated gene expression profile that follows the disease progression are implicated in the progression of the disease state and implicated in the increasing severity of the disease state. Eventually, a point is reached in the later stages in the disease where the induction of gene expression or the upregulation of gene expression is implicated as a "sick animal" response, whereby, the animals physiology is attempting to reach or bring the body back into physiological balance.

Any repression of genes are identified by comparing the gene expression profiles of the normal animal to the gene expression profile of medically relevant animal model. The gene(s) that demonstrate repression prior to the presentation of symptoms or early in the disease presentation process for the medically relevant animal model are "grouped" in the category of the maintenance of the normal or healthy state. Genes that are repressed during the progression of the disease are "grouped" in the category of the decrease of the healthy state or an increase of disease severity.

Furthermore, by comparing the gene expression profiles of the normal animal to the gene expression profile of the medically relevant animal model and the treated medically relevant animal models will continue to provide further insight to the genes that are involved in efficacy, toxicity and ADME. In general, the genes selected to be the efficacy genes are selected based on the gene expression profiles of the genes in the disease target organ. Typically, these genes are those genes that are repressed during disease development and progression and either induced or left unaltered in expression by the positive control drug. Additionally, genes that are induced during disease development and/or during disease progression or induced by the negative control drug are also selected for content on the gene expression biochips as negative parameters of efficacy.

The genes selected for toxicology and ADME are selected in a manner similar to the efficacy genes using the same previously described concepts but from the kidney, liver, central nervous system, stomach and intestine.

The comparison of the gene expression across and down these time-points and treatments are performed using a computer program as discussed supra.

Protein Expression Experiment Preparation

Animal models are randomly distributed to the same groups as described above and time points are selected for comparison of gene and protein expression between normal and diseased animals, using the same criteria as described above for gene expression. The procedure again begins with the harvesting of the organs involved in the disease or the organs afflicted by the disease (normal, diseased and treated organs). As an example, in a murine asthma model, the lungs would be the organs that are harvested. Harvested organs from each group are either randomly distributed to three sub-groups (gene expression, protein expression or standard practices) or each organ from each mouse is divided into thirds and each third is placed in one of three sub-groups (gene expression, protein expression and standard practices).

Proteins are extracted from each of the subgroups. The proteins are extracted using one of a number of different standard methods. These methods are typically a standard cell lysis method. In general, these methods involve the piece of organ or tissue being treated with digestive enzymes and solutions that contain detergents. Other methods of extracting proteins from pieces of organs involve treatment of the piece with digestive enzymes followed by repeated freezing and thawing or placing the material under high pressure after enzymatic treatment or enzymatic treatment followed by swelling the cells until they burst. Additionally, automate systems are now available that makes the extraction of proteins from biological material a high-through put process. An example of these automated systems is the Qiagen BioRobot 3000. The extracted protein is maintained in a standard method that prevents loss or degradation of the protein. One standard method of storage is as a pellet in a low adhesion plastic microfuge tube in the presence of proteinase inhibitors. Commonly the pellet is stored at −80° C. or −20° C. and sealed shut to prevent evaporation.

The extracted protein is checked for degradation, or intactness and is quantified. The standard method for quantifying a protein sample is spectrophotometrically ($A_{280}$) or through a standard chemical assay. The standard method for determining intactness of a protein is a protein gel. Examples of these protein gels are Sodium Dodecyl Sulphate Polyacrylamide gel electrophoresis (SDS-PAGE), denaturing gradient gel electrophoresis, two-dimensional gel electrophoresis (2-D Gels) and polyacrylamide gel electrophoresis (PAGE). Conversely, the intactness and quantity of the protein can be determined using one of the new "Lab-on-a-chip" systems that are available. An example of these instruments is the Agilent Bioworkstations.

From the extracted and intact proteins, protein expression profiles are determined by 2-D gel electrophoresis. The 2-D gels are performed, landmarked, analyzed (by a computer program) and compared for induced and repressed protein expression as well as for modifications to the proteins or the production of novel protein complexes. Comparison of the protein expression profiles between normal; diseased; and, diseased+treatments; at the selected time-points requires that a comparison between the different treatments and disease states at the selected time-points as well as between the different time-points be performed. The following matrix is constructed for illustrative purposes only and is not meant as a limitation to the invention.

| Disease state and treatment | | Time-points for harvesting organs | | | | | | | | | | | |
|---|---|---|---|---|---|---|---|---|---|---|---|---|---|
| Disease State | Treatment | 1 | 2 | 3 | 4 | 5 | 6 | 7 | 8 | 9 | 10 | 11 | 12 |
| Normal | None | + | + | + | + | + | + | + | + | + | + | + | + |
| Diseased | Mock | + | + | + | + | + | + | + | + | + | + | + | + |
| Diseased | Positive* | − | − | − | − | + | + | + | + | + | + | + | + |
| Diseased | Negative* | − | − | − | − | + | + | + | + | + | + | + | + |
| Diseased | Candidate 1*# | − | − | − | − | + | + | + | + | + | + | + | + |
| Diseased | Candidate 2*# | − | − | − | − | + | + | + | + | + | + | + | + |

+ Indicates that samples were harvested from the medically relevant animal model.
− Indicates that samples were not harvested from the medically relevant animal model.
*The assumption is that the first few time-points are intermediate in the expression of the disease. Therefore, the time-points are collected to study the disease and provide a baseline for the future time-point comparisons.
The number of candidate drugs in an experiment is more dependent upon the size and the ability to handle increasing numbers of samples and not the actual numbers of candidate or control drugs used in the experiment.

The protein expression profile comparisons need to occur down the columns and across the rows. As protein expression profiling occurs down the rows between normal and mock treated diseased animals, the protein's that are differentially (induced or repressed) regulated during the development of the disease, during disease progression and in the fully developed disease are revealed. Comparison of the protein profiling between time-points for the mock treated diseased control reveal protein expression that is involved in the development of the disease. The expansion of the comparisons down the rows to include the positive and negative treatments of the diseased animals identifies the proteins that are involved in the amelioration of the disease state (positive drug control) and the proteins that involved in the exacerbation or non-efficacious treatment (negative drug control) of a diseased state. The comparison of the gene and protein expression profiles between the control treatments to the diseased animal model and the treatments of the candidate drugs allows an evaluation of the candidate drugs' efficacy and toxicity.

The organs that are subjected to gene and protein expression profiling are the organs that are involved in systemic detoxification of the body, organs that are involved in the movement of the drug, organs that would be the targets of a drug's toxicity and the organs that are the target organ for the disease. As an example, in a murine asthma model the organs that are evaluated include (but not limited to) the lungs, stomach, intestine, heart, kidney, liver and the central nervous system. Thus the previous two-dimensional table becomes a multi-layered matrix composed of a table for each organ.

Proteins that are determined to be differentially expressed between two time-points or between two treatments are excised from the gel and prepared for Matrix Assisted Laser Desorption Ionization Time of Flight analysis (MALDI-TOF). The resulting data is then used to search the protein databases to determine the identity of the protein or to determine if the protein is an unknown.

Selection of protein content for the protein expression biochip occurs by selecting antibodies to proteins that fit into the categories of disease progression or development and healthy state decrease or loss. Disease progression or disease development proteins are selected based on the comparison of the normal animals protein expression profile to the mock treated diseased animals protein expression profile. Induction or upregulation of a protein's expression or proteins' expression or an alteration to the protein (e.g. phosphorylation) in a medically relevant diseased animal model is an indication that the induced or altered protein is involved with the induction of the disease state. Especially relevant are those proteins that are induced or altered early in the development of the disease before any disease symptoms can be detected or those proteins induced or altered early in the disease process. Proteins that have an induced or altered protein expression profile or an upregulated protein expression profile that follows the disease progression are implicated in the progression of the disease state and implicated in the increasing severity of the disease state. Eventually, a point is reached at a later stage in the disease where the induction or alteration of protein expression or the upregulation or alteration of protein expression is implicated as a "sick animal" response, whereby, the animal's physiology is attempting to reach or bring the body back into physiological.

Repressed proteins are identified by comparing the protein expression profiles of the normal animal to the protein expression profile of medically relevant animal model. The protein(s) that demonstrate repression prior to the presentation of symptoms or early in the disease presentation process for the medically relevant animal model are implicated in the maintenance of the normal or healthy state. Proteins that are repressed during the progression of the disease are implicated in a decrease of the healthy state or an increase of disease severity.

Furthermore, by comparing the protein expression profiles of the normal animal to the protein expression profile of the medically relevant animal model and the treated medically relevant animal models continually provides further insight to the proteins that are involved in efficacy, toxicity and ADME. The selection of the genes for these groups is partially based on their organ expression.

In general, the proteins selected to be the efficacy proteins are selected based on the protein expression profiles of the proteins in the disease target organ. Typically these proteins are the proteins that are repressed during disease development and progression and either induced or have a normal expression pattern in the expression pattern of the positive control drug time-points. Additionally, proteins that are induced or altered during disease development and/or during disease progression or induced or altered by the negative control drug can be selected for content on the protein expression biochips as negative parameters of efficacy.

The proteins selected for toxicology and ADME are selected in a manner similar to the efficacy genes using the same previously described concepts but from the kidney, liver, central nervous system, stomach and intestine.

Data obtained from the biochips are inputted into the DGPB database and analyzed as described supra.

Design of the PMEET-ADME Gene and Protein Expression Biochips.

Part A: Design of the Gene Expression Biochips

The gene and protein expression biochips allow for the evaluation of the efficacy, toxicity, absorption, distribution, metabolism and elimination of a tested drug as described above. In general, the genes for the gene expression biochips are oligonucleotides of a defined length; have similar hybridization characteristics; lack lengthy complementary regions; and, should not form hairpins. For the hybridization characteristics to be similar across a wide range of oligonucleotides requires that the oligonucleotides be of the same length, have a similar percentage of Guanine to Cytosine content and lack any extensive runs of poly A, poly G, poly C or poly T tracts. The goal of having these parameters is to produce oligonucleotides that have similar melting and hybridization temperatures. Oligonucleotides can be designed using commercially available software, using the stipulated parameters or stipulate parameters. Examples of such software are "MacVector" and "Oligo". Production of the oligonucleotides is accomplished by using a DNA synthesizer followed by purification of the oligonucleotides using an HPLC equipped with an UV detector and a fraction collector. Finally, the sequence and length of oligonucleotides is verified using a mass based method and instruments (e.g. MALDI-TOF analysis).

The purified and verified oligonucleotides are spotted onto a microscope slide coated with a low adhesion hydrophilic surface or covalently attached to the surface of the microscope slide (low adhesion hydrophilic surface) using standard chemistry conjugation chemistry. The gene expression biochip is designed in a grid and quadrant fashion using positive control genes at the corners of the grids for alignment and identification of the grids. The positive control genes are genes that are not expressed or are not present in the animal kingdom, for example, oligonucleotides generated from the gene sequence of a plant gene or artificially designed oligonucleotides. In this format, the labeled complementary positive control can be spiked into the hybridization buffer during the gene expression biochip hybridization experiments. Additional controls include positive and negative experimental controls. The positive experimental controls are controls for genes that are expected to be present and expressed in the RNA extracted from the harvested organs. As an example, all or some of the housekeeping genes (e.g. GAPDH and Actin) are used as positive experimental controls. Negative experimental control genes are genes that are not found in the animal kingdom and serve the function of providing an evaluation of the amount of background or non-specific hybridization occurring. The positive controls provide experimental evidence that the hybridization experiment was successful.

Spotting of the oligonucleotides to a microarray slide is performed using the methods described in the detailed description of the invention, supra. The primary oligonucleotide grid is replicated many times on the same slide so as to provide several experimental replicates per PMEET-ADME gene expression hybridization experiment.

Design of the Protein Expression Biochips

The content of the protein expression biochips are antibodies specific for the differentially expressed proteins (See Tables 1-5 for examples of antigens to which antibodies can be generated against for use in the protein expression biochip), or any other molecule that binds selectively with the target protein, as discussed in the detailed description of the invention.

There are a variety of methods and sources that are used to obtain the required antibodies. These antibodies can be from commercial sources, or are generated in-house using standard immunization and antibody purification procedures, such as standard hybridoma techniques; using the Abginex Xenomouse; phage display techniques; or, using a combination of animal immunization (e.g. mouse, rat, donkey, chicken, etc.) and phage display. The antibodies are conjugated (using standard conjugation chemistry) to a microarray solid support.

The protein expression biochip is designed to comprise positive control antibodies, experimental positive control antibodies and negative control antibodies. The positive control antibodies are to molecules that occur ubiquitously throughout the cells of an animal, such as housekeeping proteins such as GAPDH or Actin, and are spiked into the protein expression biochip experimental binding solution. The negative control antibodies are to haptens that do not exist naturally. Antibodies are detected using digoxigenin or are fluorescently labeled (FITC). The antibodies are attached to known locations in a grid format so as to provide landmarks and identification points for the locations of the antibodies. Each of these grid formats are repeated many times on the PMEET-ADME protein expression biochip so as to provide several experimental replicates per PMEET-ADME protein expression experiment.

Metabolic Profiling

Part A: Testing and Evaluation of Biological Fluids and Biological Materials

The testing and evaluation of the biological fluids are conducted according to the standard techniques and procedures that are involved in the typical clinical testing of biological fluids. These tests include urine analysis, blood analysis, analysis of central nervous system fluids and the testing of fecal material.

Part B: Testing and Evaluation of Drug Metabolites

The testing and evaluation of drug metabolites is conducted according to the standard techniques and procedures that are involved in the determination of drugs and drug metabolites in the blood of an animal. These tests include the testing of hair samples, fingernail, toenail, urine, blood and saliva.

PMEET-ADME Score Development and Determination

Part A: Development of Scoring System for the Gene Chip

The scoring system for the PMEET-ADME gene expression chip is a system based on the signal intensity from an oligonucleotide and the importance of the gene in the PMEET-ADME system. The scoring system is a weighted scoring system that takes into consideration the involvement of a gene in the efficacy, toxicity and ADME process and the intensity or the level of expression of that gene in that sample for that portion of the PMEET-ADME experiment. As an example, genes that have been determined to be implicated in disease development or disease progression are weighted in proportion to their involvement in disease development or progression and scored negatively as expression increases above normal levels. The genes that are implicated in efficacy are weighted with respect to their impact upon the development or maintenance of the normal physiological state except that these genes are assigned a positive score as their expression increased over normal expression. Thus, by providing a weighted scoring system for the genes based on their impact in the maintenance of a physiological state and the scoring of these genes' expression as either negative or positive, an overall PMEET-ADME score can be produced for the gene expression biochip.

Part B: Development of Scoring System for the Protein Chip

The scoring system for the PMEET-ADME protein expression chip is the same as described above, but based on the signal intensity from an antibody and the importance of the protein in the PMEET-ADME system. The scoring system is a weighted scoring system that takes into consideration the involvement of a protein or the alteration of a protein in the efficacy, toxicity and ADME process and the intensity or the level of expression of that protein or alteration of that protein in that sample for that portion of the PMEET-ADME experiment. As an example, proteins that have been determined to be implicated in disease development or disease progression are weighted in proportion to their involvement in disease development or progression and scored negatively as expression increases above normal levels. The proteins that have been implicated in efficacy are weighted with respect to their impact upon the development or maintenance of the normal physiological state except that these genes are assigned a positive score as their expression increased over normal expression. Thus, by providing a weighted score system for the proteins based on their impact in the maintenance of a physiological state and the scoring of these proteins' expression as either negative or positive, an overall PMEET-ADME score can be produced for the protein expression biochip.

Part C: Development of PMEET-ADME Scoring System

The combination of the PMEET-ADME gene expression and protein expression score requires an evaluation of the genes and proteins involved in the different process of efficacy, toxicity, ADME, disease progression and disease development. The scores from the PMEET-ADME gene and protein expression experiments are weighted and the two scores are combined to produce a single combined PMEET-ADME score.

Example 1

PMEET-ADME Gene and Protein Expression

Animals are randomly distributed to the following groups: Control (No-disease); Diseased mock treatment control (drug vehicle only); Diseased positive treatment control (Positive drug treatment); Diseased negative treatment control (Negative drug treatment); Diseased candidate treatment(s) (Candidate drug treatment groups).

Animals are sacrificed at different time points of disease progression. The first time point is at the initial phase of the medically relevant disease, at several intermediate timepoints during the progression of the disease, and the final time point is during the full-blown disease state. The organs involved in the disease or the organs afflicted by the disease (normal, diseased and treated organs) are harvested. As an example, in a murine asthma model, the lungs are harvested. Harvested organs from each group are randomly distributed to three sub-groups (gene expression, protein expression or standard practices) or each organ from each mouse is divided into thirds and each third is placed in one of three sub-groups (gene expression, protein expression and standard practices).

RNA from each of the subgroups is extracted. Extraction methods used, but are not limited to, are the Cesium Chloride cushion method, the Acid-Phenol method, the Tri-Sol® method and numerous different column extraction methods or solid support extraction methods (e.g. RNAeasy® from Qiagen). Additionally, automated systems are also used that makes the extraction of nucleic acids from biological material a high-through put process. Examples of these systems include the ABI 6700 Nucleic Acid WorkStation, the Roche Magna Pure system, the Qiagen BioRobot 3000 system and the Gentra systems nucleic acid extractor. The extracted RNA is maintained in a standard method that prevents loss or degradation of the RNA. One standard method for this is as a precipitated pellet in a plastic microfuge tube that has low nucleic acid adhesion. Commonly the pellet is stored under 100% Ethanol at −80° C. and sealed shut to prevent evaporation.

Once all of the RNA in gene expression subgroup, has been extracted from each control and treatment group from a single time-point, the individual subgroup samples are checked for degradation, and the quantity of the RNA is determined. The standard method for quantifying a nucleic acid sample has been described above.

From the extracted and intact RNA, a first strand cDNA synthesis is synthesized by using any one of the standard procedures described above. The first strand synthesis cDNA is generated from total RNA or from mRNA. In the second case (mRNA) the poly A+ fraction of the total RNA is purified using the standard technique of Oligo dT column purification or using one of the many commercial kits that are available.
A) During the first strand synthesis reactions the nucleic acid, the cDNA, is labeled through the incorporation of fluorescent nucleotides.
B) Alternatively, the cDNA can be labeled using a chemical labeling method such as the Roche Molecular Biochemicals Biotin Chem-link and the DIG chem-link systems.
C) The total RNA or the poly A+ mRNA can be labeled using a chemical labeling method.

These oligonucleotides are then applied to the PMEET-ADME gene expression biochip. In general, this experiment is carried out for each of the time-points and treatment groups by using an aliquot of the labeled normal nucleic acid, an aliquot of the experimental nucleic acid, an aliquot of the positive controls with a standard hybridization buffer. Alternative hybridization buffers could be used in place of the standard hybridization buffer. These alternatives are generated by using different salts in the hybridization buffer, the addition of hybridization accelerators, addition of chemicals and proteins to reduce non-specific hybridization and/or the addition of chemicals and proteins to increase the specificity of hybridizations. The combined hybridization mixture is heat denatured, quick cooled on ice and placed onto the PMEET-ADME gene expression microarray, commonly within a hybridization chamber, and incubated at the predetermined hybridization temperature for a period of time, usually overnight. The next day the hybridization solution is removed and the gene expression microarray is washed in solutions of decreasing salt concentrations (increasing stringency) and in the presence of elevated temperatures. These washes remove all of the unbound normal and experiment nucleic acids (reduce background and remove excess labeled nucleic acids).

The intensity of the labeled nucleic acids at an oligonucleotide location is determined by using a commercial available reader and software system. As examples of a reader and software package, the GSI Lumonics reader and the Scanlytics software program.

Once all of the time-points and treatment groups are compared to normal, the PMEET-ADME score is determined.

With respect to PMEET-ADME protein expression, the protocols described above are followed, with the exception that antibodies are immobilized on the PMEET-ADME chip.

The proteins from the animal model experimental groups are extracted from each of the subgroups. The proteins are extracted using one of a number of different standard methods. These methods are typically a standard cell lysis method. In general, these methods involve the piece of organ or tissue being treated with digestive enzymes and solutions that contain detergents. Other methods of extracting proteins from pieces of organs involve treatment of the piece of organ or tissue with digestive enzymes followed by repeated freezing and thawing; or placing the material under high pressure after enzymatic treatment; or enzymatic treatment followed by swelling of the cells until they burst. Additionally, automate systems are now available that makes the extraction of proteins from biological material a high-through put process. An example of these automated systems is the Qiagen BioRobot 3000.

The proteins are prepared for the PMEET-ADME protein expression chip by labeling with a fluorescent dye attached to a chemical linker that has an NHS ester for the labeling of proteins through the free amino groups present in the individual proteins. An aliquot of the labeled protein is mixed into the protein-binding buffer and the mixture is placed onto the PMEET-ADME protein expression chip. Each time-point and treatment group is assayed in this manner and the data collected for evaluation by the PMEET-ADME scoring system.

All data obtained from any experiment is inputted into the DGPB database for analysis and evaluation.

Generation of Biochips for Evaluation of PMEET-ADME in Humans

PMEET-ADME gene and protein expression biochips are generated for humans by using gene and protein databases, gene and protein alignment programs and gene and protein similarity comparison programs. The genes and proteins that make up the content for the Medically Relevant Animal Models gene and protein expression biochips are used to search the human gene and protein database(s) to find similar genes and proteins. These human genes and the antibodies to these human proteins are then used to provide content for Human gene and protein expression PMEET-ADME biochips. These human chips are useful in FDA phase I, II and III trials to evaluate an individuals response to the treatment. Additionally, human biochips many eventually provide diagnostic and therapeutic biochips for the evaluation of patients.

The invention has been described in detail with reference to preferred embodiments thereof. However, it will be appreciated that, upon consideration of the present specification and drawings, those skilled in the art may make modifications and improvements within the spirit and scope of this invention as defined by the claims.

What is claimed is:

1. A biochip array for evaluating the effect of a composition for the treatment of at least one human disease, said biochip array comprising a surface and a plurality of molecules stably attached to said surface, wherein said plurality of molecules are capable of selective binding to at least one member of the group consisting of DNA, RNA, proteins, peptides and fragments thereof, said at least one member being representative of an animal model for the at least one human disease, said plurality of molecules being derived from said animal model having been treated with said composition.

2. The biochip array of claim 1 wherein said member is provided from any metabolic pathway; apoptotic pathway; inflammatory pathway; cytokine production pathway; cellular growth product pathways; proto-oncogenes; oncogenes; antibodies or fragments thereof provided by the animal model.

3. The biochip array of claim 1, wherein the at least one human disease is allergy, arthritis, inflammatory disease, cancer, a disease caused by external environmental influences, or a stress-related disease.

4. The biochip array of claim 1, wherein the plurality of molecules comprises gene fragments from any part of a gene or several parts of the same gene, whole genes, nucleic acids, proteins or fragments thereof, or peptides or fragments thereof, from the animal model.

5. A biochip array for evaluating the effect of a composition for the treatment of at least one human disease, said biochip array consisting essentially of a surface and a plurality of molecules stably attached to said surface, wherein said plurality of molecules are capable of selective binding to at least one member of the group consisting of DNA, RNA, proteins, peptides and fragments thereof, said at least one member being representative of an animal model for the disease, said plurality of molecules being derived from said animal model having been treated with said composition.

6. A biochip array for evaluating the effect of a composition for the treatment of at least one human disease, said biochip array consisting of a surface and a plurality of molecules stably attached to said surface, wherein said plurality of molecules are capable of selective binding to at least one member of the group consisting of DNA, RNA, proteins, peptides and fragments thereof, said at least one member being representative of an animal model for the disease, said plurality of molecules being derived from said animal model having been treated with said composition.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: This polypeptide with 4 amino acids can be
      synthesized and then modified
<220> FEATURE:
<221> NAME/KEY: Modified-site
```

```
<222> LOCATION: (1)..(1)
<223> OTHER INFORMATION: The N-terminal amino acid is formylated.

<400> SEQUENCE: 1

Met Leu Phe Phe
1
```